United States Patent
Gruber et al.

(10) Patent No.: US 9,222,902 B2
(45) Date of Patent: Dec. 29, 2015

(54) ESTIMATIONS OF NUCLEAR MAGNETIC RESONANCE MEASUREMENT DISTRIBUTIONS

(75) Inventors: Fred K. Gruber, Boston, MA (US);
Lalitha Venkataramanan, Lexington, MA (US); Tarek M. Habashy, Burlington, MA (US); Philip M. Singer, Cambridge, MA (US); Denise E. Freed, Newton Highlands, MA (US)

(73) Assignee: Schlumberger Technology Corporation, Sugar Land, TX (US)

( * ) Notice: Subject to any disclaimer, the term of this patent is extended or adjusted under 35 U.S.C. 154(b) by 772 days.

(21) Appl. No.: 13/346,468

(22) Filed: Jan. 9, 2012

(65) Prior Publication Data
US 2013/0179083 A1    Jul. 11, 2013

(51) Int. Cl.
| | | |
|---|---|---|
| G01V 1/40 | (2006.01) | |
| G01N 24/08 | (2006.01) | |
| G01R 33/44 | (2006.01) | |
| G01V 3/18 | (2006.01) | |

(52) U.S. Cl.
CPC ............ *G01N 24/081* (2013.01); *G01R 33/448* (2013.01)

(58) Field of Classification Search
CPC ....... G01V 3/175; G01V 3/32; G01R 33/448; G01N 24/081
USPC .................................................... 702/13–18
See application file for complete search history.

(56) References Cited

U.S. PATENT DOCUMENTS

| | | |
|---|---|---|
| 5,023,551 A | 6/1991 | Kleinberg et al. |
| 5,363,041 A | 11/1994 | Sezginer |
| 6,225,803 B1 | 5/2001 | Chen |
| 6,462,542 B1 | 10/2002 | Venkataramanan et al. |
| 7,286,937 B2 | 10/2007 | Goswami et al. |
| 2002/0175682 A1 | 11/2002 | Chen et al. |
| 2004/0066194 A1 | 4/2004 | Slade et al. |
| 2005/0104587 A1 | 5/2005 | Akkurt |
| 2007/0114996 A1 | 5/2007 | Edwards |
| 2010/0268753 A1 | 10/2010 | Fujiwara et al. |
| 2013/0060474 A1 | 3/2013 | Venkataramanan et al. |

OTHER PUBLICATIONS

Venkataramanan et al., "Mellin Transformation of CPMG data", Journal of Magnetic Resonance, 2010, vol. 206: pp. 20-31.*
Kleinberg et al., "SPE 26470: Nuclear Magnetic Resonance of Rocks: T1 vs. T2," SPE International, 1993: pp. 553-563.

(Continued)

*Primary Examiner* — Phuong Huynh
(74) *Attorney, Agent, or Firm* — Jakub Michna

(57) ABSTRACT

A nuclear magnetic resonance (NMR) related distribution is estimated that is consistent with NMR measurements and uses linear functionals directly estimated from the measurement indications by integral transforms as constraints in a cost function. The cost function includes indications of the measurement data, Laplace transform elements and the constraints, and a distribution estimation is made by minimizing the cost function. The distribution estimation may be used to find parameters of the sample. Where the sample is a rock or a formation, the parameters may include parameters such as rock permeability and/or hydrocarbon viscosity, bound and free fluid volumes, among others. The parameters may be used in models, equations, or otherwise to act on the sample, such as in recovering hydrocarbons from the formation.

19 Claims, 10 Drawing Sheets

(56) References Cited

OTHER PUBLICATIONS

Hurlimann et al., "Quantitative Measurement of Two-Dimensional Distribution Functions of Diffusion and Relaxation in Grossly Inhomogeneous Fields," Journal of Magnetic Resonance, 2002, vol. 157: pp. 31-42.
Borgia et al., "A Robust Method for Calculating Geometric Mean Times from Multiexponential Relaxation Data, Using Only a Few Data Points and Only a Few Elementary Operations," Magnetic Resonance Imaging, 1996, vol. 14(7/8): pp. 895-897.
Borgia et al., "A Method for Approximating Fractional Power Average Relaxation Times Without Inversion of Multiexponential Relaxation Data," Magnetic Resonance Imaging, 1998, vol. 16(5/6): pp. 625-627.
Borgia et al., "Estimates of Permeability and Irreducible Water Saturation by Means of a New Robust Computation of Fractional Power Average Relaxation Times," Magnetic Resonance Imaging, 198, vol. 16 (5/6): pp. 613-615.
Borgia et al., "Different 'average' nuclear magnetic resonance relaxation times for correlation with fluid-flow permeability and irreducible water saturation in water-saturated sandstones," J. Appl. Phys., Nov. 1997, vol. 82.(9): pp. 4197-4204.
Freed, "Scaling Laws for Diffusion Coefficients in Mixtures of Alkanes," Physical Review Letters, Feb. 2005, vol. 94: pp. 067602-1-067602-4.
Freed, "Dependence on Chain Length of NMR Relaxation Times in Mixtures of Alkanes," The Journal of Chemical Physics, 2007, vol. 126: pp. 174502-1-174502-10.
Kleinberg, "Well Logging," Encyclopedia of Nuclear Magnetic Resonance, vol. 8 Tis-Z Indexes, John Wiley & Sons: New York, 1996: pp. 4960-4969.
Kleinberg et al., "SPE 38737: Tapered Cutoffs for Magnetic Resonance Bound Water Volume," SPE International, 1997: pp. 197-202.
Allen et al., "How to Use Borehole Nuclear Magnetic Resonance," Oilfield Review, Summer 1997: pp. 34-57.
Fordham et al., "Imaging Multiexponential Relaxation in the (y, log e T1) Plane, with Application to Clay Filtration in Rock Cores," Journal of Magnetic Resonance, Series A, 1995, vol. 113: pp. 139-150.
Venkataramanan et al., "Solving Fredholm integrals of the first kind with tensor product structure in 2 and 2.5 dimensions," IEEE Transactions on Signal Processing, May 2002, vol. 50(5): pp. 1017-1026.
McWhirter et al., "On the Numerical Inversion of the Laplace transform and similar Fredholm Integral Equations of the First Kind," J. Phys. A: Math. Gen., 1978, vol. 11(9): pp. 1729-1745.
Epstein et al., "The Bad Truth About Laplace's transform," SIAM Review, 2008, vol. 50: pp. 1-18.
Venkataramanan et al., "Mellin Transform of CPMG data," Journal of Magnetic Resonance, 2010, vol. 206: pp. 20-31.
Butler et al., Estimating Solutions of the First Kind Integral Equations with Nonnegative constraints and optimal smoothing,: SIAM J. Numer. Anal., Jun. 1981, vol. 18(3): pp. 381-397.
Press et al., "19.5: Linear Regularization Methods," and "19.6: Backus-Gilbert Method," Numerical Recipes in C, Third Edition, Cambridge University Press: New York, 1992: pp. 1006-1016.
Song et al., "T1-T2 Correlation Spectra Obtained Using a Fast Two-Dimensional Laplace Inversion," Journal of Magnetic Resonance, 2002, vol. 154: pp. 261-268.
Heaton et al., "4D NMR—Applications of the Radial Dimension in Magnetic Resonance Logging," Petrophysics, Apr. 2008, vol. 49(2): pp. 172-186.
Hurlimann et al., "Hydrocarbon Composition from NMR Diffusion and Relaxation Data," Petrophysics, Apr. 2009, vol. 50(2): pp. 116-129.
Prudnikov et al., "Chapter 2.1.: The Power of Algebraic Functions," Integrals and Series: vol. 5 Inverse Laplace Transforms, Gordon and Breach Science Publishers: Philadelphia, 1992: p. 11.
Wen Shen, Lecture Notes for Laplace Transform, Apr. 2009 pp. 1-23.
William H. Press et al., Numerical Recipes in C: The Art of Scientific Computing, 1992, pp. 788-819, Second Edition, Cambridge University Press.

* cited by examiner

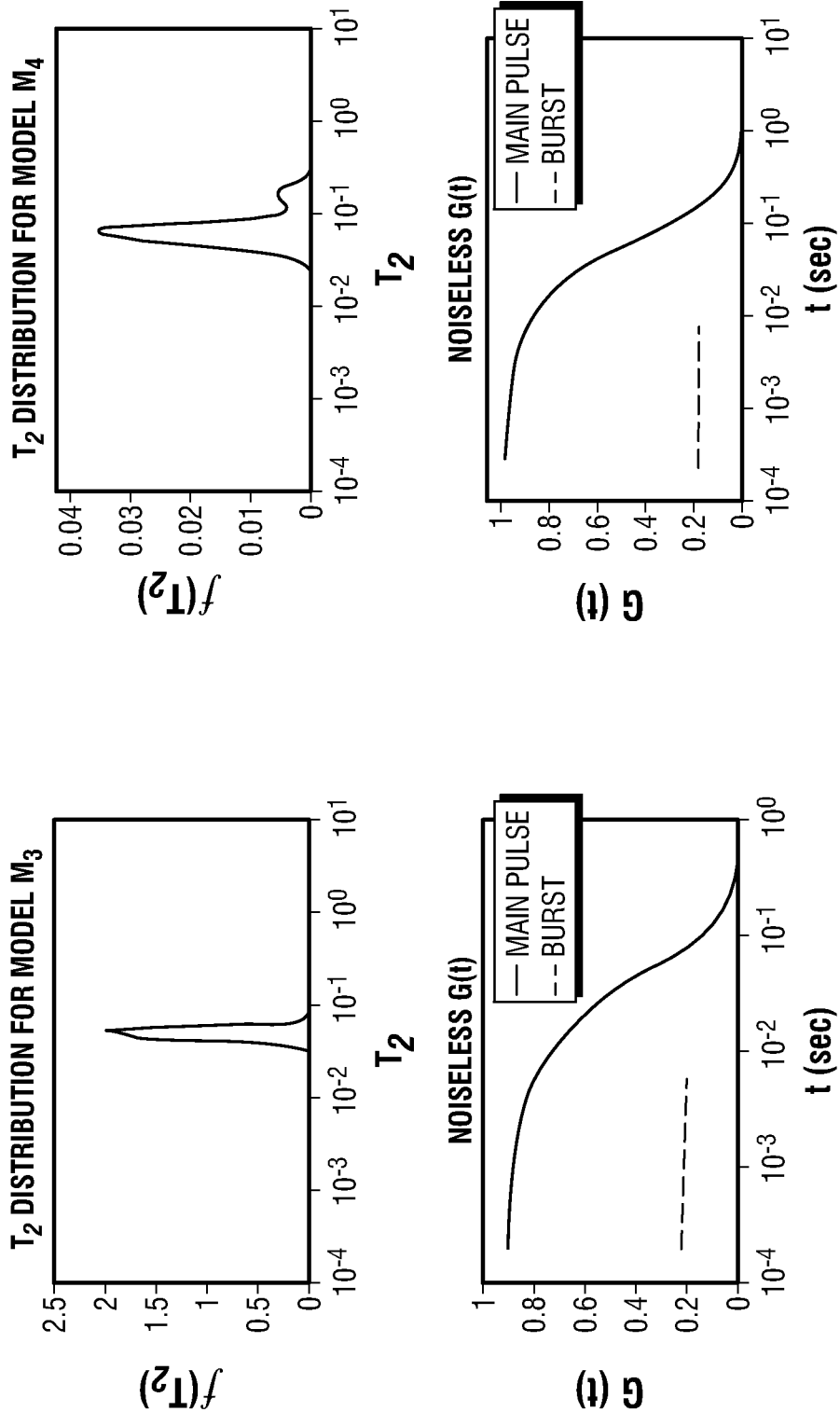

ESTIMATIONS OF NUCLEAR MAGNETIC RESONANCE MEASUREMENT DISTRIBUTIONS

This application is related to and hereby incorporates by reference herein in its entirety co-owned U.S. Pat. No. 6,462,542 to Venkataramanan et al., entitled "Nuclear Magnetic Resonance Measurements and Methods of Analyzing Nuclear Magnetic Resonance Data," and U.S. Ser. No. 13/333,232 to Venkataramanan et al., entitled "Estimation of Petrophysical and Fluid Properties Using Integral Transforms in Nuclear Magnetic Resonance," filed on Dec. 21, 2011.

BACKGROUND

The statements made herein merely provide information related to the present disclosure and may not constitute prior art, and may describe some embodiments illustrating the invention.

Measured nuclear magnetic resonance (NMR) data resulting from a multi-component sample can be denoted by G(t) which represents a multi-exponential decay, with time constants $T_2$ and amplitudes $f(T_2)$ $$G(t) = \int_0^\infty P_\tau(T_2) e^{-t/T_2} f(T_2) dT_2 \quad (1)$$

where the function $P_\tau(T_2)$ is referred to as the polarization factor and depends on the pulse sequence of the NMR equipment used to probe and measure the sample.

In certain samples containing hydrocarbons and water, e.g., geological formations, the transverse relaxation time $T_2$ is the characteristic de-phasing time for protons in hydrocarbons or water present in pores of a rock or in the bulk fluid. As aforementioned, the function $P_\tau(T_2)$ of equation (1) depends on the pulse sequence of the NMR equipment used to probe and measure the sample. For example, $$P_\tau(T_2) = \begin{cases} 1 & \text{CPMG pulse sequence with full polarization} \\ 1 - 2e^{-\tau/T_2} & \text{inversion recovery} - \text{CPMG pulse sequence} \\ 1 - e^{-\tau/T_2} & \text{saturation recovery} - \text{CPMG pulse sequence} \end{cases} \quad (2)$$

where τ is a function of pre-polarization time and longitudinal relaxation, and CPMG refers to the well-known Carr-Purcell-Meiboom-Gill sequence. In downhole applications, the function $P_\tau(T_2)$ is a complex function of tool geometry (such as length of magnet and design of RF antenna), operational constraints (such as cable speed) as well as the pulse sequence.

In equation (1) the $T_2$ distribution denoted by $f(T_2)$ is estimated from indications of the measured data G(t). The conventional approach to estimating $f(T_2)$ utilizes an inverse Laplace transform (ILT), See L. Venkataramanan et al., "Solving Freholm integrals of the first kind with tensor product structure in 2 and 2.5 dimensions", *IEEE Transactions on Signal Processing*, 50:1017-1026, 2002. More particularly, it is assumed that the indications of data G(t) are measured with additive, white, Gaussian noice. Traditionally, assuming $P_\tau(T_2)$ is known, an inversion algorithm is used to estimate the distribution of relaxation times $f(T_2)$ in equation (1) from the measured data indications G(t). Next, linear functionals of the estimated $f(T_2)$ can be used to estimate the petro-physical or fluid properties. For example, the area under the $T_2$ distribution can be interpreted as the porosity of the rock. Often, based on lithology, a threshold $T_2$ is chosen as the cut-off characteristic time separating fluid bound to the pore surface and fluid that is not bound to the pore surface and flow more easily. For example, in sandstones, the area under the $T_2$ distribution corresponding to relaxation times smaller than 33 msec has been empirically related to bound fluid volume. The remaining area under the $T_2$ distribution corresponds to free fluid volume. The mean of the distribution $\langle \ln T_2 \rangle$, is empirically related to either rock permeability and/or to hydrocarbon viscosity. The width of the distribution, $\sigma_{ln(T_2)}$, provides a qualitative range of the distribution of pore sizes in the rock. Moments of relaxation time or diffusion are often related to rock permeability and/or hydrocarbon viscosity. Similar answer products can also be obtained from linear functionals computed from two-dimensional diffusion-relaxation data or $T_1$-$T_2$ relaxation data.

It is well known in the literature that estimation of $f(T_2)$ is an ill-conditioned and non-linear problem. Small changes in the indications of measured data G(t) due to noise can result in widely different $f(T_2)$. In theory, there are infinitely many $f(T_2)$ that fit the data; i.e., there are non-unique solutions. In the literature, this problem is addressed by introducing a choosing the "smoothest" solution $f(T_2)$ that fits the data. More particularly, a regularization functional is introduced, and the solution is estimated through minimization of a cost function Q with respect to the underlying distribution f, $$Q = \|G - Lf\|^2 + \alpha \|f\|^2 \quad (3)$$

where G is a vector representing the measured data, L is the matrix of the discretized function $P_\tau(T_2)e^{-t/T_2}$, and f is the discretized version of the underlying density function $f(T_2)$. The first term in the cost function is the least squares error between the data and the fit from the model in equation (1). The second term is referred to as the regularization and incorporates smoothness in the relaxation amplitudes into the problem formulation. The parameter α denotes the compromise between the fit to the data and an a priori expectation of the distribution. In equation (3), α is the weight given to the regularization and can be chosen by a number of different methods.

Previously incorporated U.S. Ser. No. 13/333,232 describes a method based on integral transforms that allows direct computation of a linear functional of $f(x)$ (where the variable x may be the transverse relaxation time ($T_2$), the longitudinal relaxation time ($T_1$), Diffusion (D), any of various two-dimensional data sets (such as D-$T_2$ or D-$T_1$ or $T_1$-$T_2$), multi-dimensional data sets (such as D-$T_2$-$T_1$, D-$T_2$-$T_1$-azimuth, D-$T_2$-$T_1$-different depth of investigations) without involving computation of $f(x)$. The central idea of this approach is to compute the integral transform of G(t) using a function k(t) such that the Laplace transform of k(t) denoted by K($T_2$) has the desired properties in the x domain (hereinafter for simplicity purposes described with respect to the $T_2$ domain). Let the integral transform of the data indications G(t) be denoted by $\Im\{G(t)\} = A$, such that $$\Im\{G(t)\} = A = \int_0^\infty k(t) G(t) dt \quad (4)$$

From equations (1) and (4), $$A = \int_0^\infty K(T_2) P_\tau(T_2) f(T_2) dT_2 \quad (5)$$

where the functions k(t) and K($T_2$) form a Laplace-transform pair, with $$K(T_2) = \int_0^\infty k(t) e^{-t/T_2} dt \quad (6)$$

From the right hand side of equation (5), for a desired linear transformation in the $T_2$ domain, the integral transform approach constructs a function k(t) in the time-domain, so that the scalar product of the function with the measured data provides A, the parameter of interest.

Using this approach, direct computation of linear functionals of the $T_2$ distribution may be made without use of the ILT method. For example, as described in previously incorporated U.S. Ser. No. 13/333,232, the Mellin, Exponential Haar, and Fourier-Mellin transform of magnetization data can be used to estimate moments, tapered areas, and the porosity of the distribution directly from the measured data.

More particularly, consider measured CPMG data G(t), its corresponding and unknown distribution $f(T_2)$, and a tapered transition $K(T_2)$ for computing the desired tapered area of the $T_2$ distribution. The function k(t) corresponding to this tapered function $K(T_2)$ may be shown. This function k(t) can be found using multiple methods: (1) using either an analytical form for k(t) (examples of this is shown in Table A), (2) using a numerical approach, (3) using a method of successive approximations, and/or (4) using convolution analysis. All these methods are described below. Once k(t) is estimated, a scalar product of k(t) with G(t) directly provides the tapered area A. Since this approach does not involve solving for $f(T_2)$ and then estimating $\int_0^\infty K(T_2)f(T_2)dT_2$, it is more straightforward and not susceptible to the subjectivity of traditional algorithms that involve inversion of an ill-conditioned and non-linear problem.

As discussed below, given a desired $K(T_2)$, the function k(t) can be computed in four ways: often, it can be computed analytically or numerically. It can also be computed using the method of successive approximations to $K(T_2)$. An alternate method of computing it involves taking advantage of the convolution-multiplication equivalence between the time and T2 domain. All four methods are described below.

For a desired $K(T_2)$, when the function k(t) exists analytically or can be computed numerically, the parameter A is obtained from equation (5). However, the function k(t) may not exist $\forall K(T_2)$. When it exists, it may also have infinite energy which can be related to infinite uncertainty in the estimated parameter A leading to instability in computing the parameter. Thus, the integral transform approach can provide insight into what linear functionals of the $T_2$ distribution can be directly applied to the data G(t) and are stable in the context of providing low uncertainty in A.

The uncertainty in A can be quantified as a function of the signal-to-noise ratio (SNR) in the measured data. Let $\sigma_\epsilon$ denote the standard deviation of the additive white Gaussian noise in the data. Equation (5) can be computed in the discrete-time domain as $$A = t_E \Sigma_{n=0}^N k(nt_E) G(nt_E) \tag{6a}$$

where $t_E$ denotes the sampling time or echo spacing. Therefore, $$\sigma_A^2 = \sigma_\epsilon^2 t_E [\Sigma_{n=0}^N k^2(nt_E) t_E] \tag{6b}$$

Equation 6b shows that when the function k(t) is square integrable, i.e, k(t) has finite energy E, where $E = \int_0^\infty k^2(t)dt$, then the uncertainty in A is always finite and directly related to the uncertainty in the measurement.

In the sub-sections below, tables are described of integral transforms developed for different polarization factors $P_\tau T_2$ encountered in oilfield NMR applications.

A. Tapered Areas from Fully Polarized Data

Consider NMR data that have been fully polarized, with $P_\tau(T_2) = 1 \forall T_2$. In this sub-section, a few integral transforms are described where $K(T_2)$ corresponds to tapered and sharp Heaviside functions.

Let $T_c$ denote the $T_2$ relaxation time at which the desired cut-off of the tapered Heaviside function is 0.5. The parameter $T_c$ is user-specified and may come from laboratory study of rock and fluid properties or may correspond to a value of $T_2$ expected to separate two fluids in the $T_2$ domain. For example, in sandstones and carbonates, the area under the $T_2$ distribution corresponding to relaxation times smaller than 33 and 100 msec, respectively, has been empirically related to bound fluid volume. Thus, given a value of $T_c$, a tapered or sharp Heaviside function $K(T_2, T_c)$ is sought such that the tapered area can be computed in the time-domain using the corresponding function $k(t, T_c)$. The integral transform for computing tapered and sharp transitions should satisfy the following properties:

1. The function $k(t, T_c)$ should exist $\forall t$ and $K(T_2, T_c)$ should exist $\forall T_2$.

2. Based on the underlying petrophysics, it is desirable that $K(T_2, T_c)$ be monotonic between 0 and 1 (on the y-axis), with $$K(T_2, T_c)|_{T_2=0} = 0 \tag{6c}$$

$$\lim_{T_2 \to \infty} K(T_2, T_c) = 1 \tag{6d}$$

$$K(T_2, T_c)|_{T_2=T_c} = 0.5 \tag{6e}$$

3. It should be possible to adjust the slope m in the $\log(T_2)$ space of the transition region, with $$m \equiv \left(\frac{dK(T_2, T_c)}{d\log T_2}\right)\bigg|_{T_2=T_c} \tag{6f}$$

In most oilfield applications, the desired slope varies from m=0.4 for gradual tapered cut-offs to m=4 for sharp cut-offs.

Using analytical means a set of integral transforms are developed that satisfy these properties, and they are summarized in Table A. For ease of reference, suggested names for the transforms are provided based on the function k(t). The energy for some of the transforms is infinity, implying infinite uncertainty in the estimated area. This energy can be decreased by several methods. One such method involves multiplication of the function k(t) by an exponential decaying signal in the time domain. A second method involves restricting the integral transform to a finite time-period. Both methods decrease the energy considerably while also reducing the slope in the transition region. For e.g., as shown in Table A, the Haar transform (HT) (row 3) has infinite energy. On the other hand, the energy of an exponential Haar transform (EHT) (row 5) is finite.

From equation (7), a desired uncertainty in the estimated area $\sigma_A$ can be translated to a desired and finite energy in the function. This finite energy can be achieved by suitable choice of parameters of the transform satisfying both the energy criteria as well as properties 1-3 described above. For example, when the desired energy for the EHT is $$\frac{2}{\pi T_c},$$

then me parameters C, $\alpha$ and $\beta$ take values provided in the following table.

TABLE A

Integral transforms that give rise to tapered transitions in the $\log(T_2)$ domain

| $K(T_2, T_c)$ | Parameters | $k(t, T_c)$ | E | m | Name of Transform |
|---|---|---|---|---|---|
| $\frac{2}{\pi}\tan^{-1}(\alpha T_2)$ | $\alpha = \frac{1}{T_c}$ | $\frac{2}{\pi}\frac{\sin(\alpha t)}{t}$ | $\frac{2}{\pi T}$ | 0.32 | Sinc |
| $\frac{T_2}{\alpha}\tanh\left(\frac{\alpha}{T_2}\right)$ | $\alpha = \frac{T_c}{0.52219}$ | $\frac{1}{\alpha}(-1)^n$ $2n\alpha < t < 2(n+1)\alpha$ | $\infty$ | 0.42 | Haar |
| $\dfrac{\alpha^2}{\alpha^2 + \dfrac{1}{T_2^2}}$ | $\alpha = \frac{1}{T_c}$ | $\alpha \sin(\alpha t)$ | $\infty$ | 0.5 | Sine |
| $\dfrac{C}{\left(\dfrac{1}{T_2}+\beta\right)}\tanh\left[\alpha\left(\dfrac{1}{T_2}+\beta\right)\right]$ | $C = \dfrac{0.7213}{T_c}$ $\alpha = (1.572)T_c$ $\beta = \dfrac{0.4087}{T_c}$ | $C(-1)^n e^{-\beta t}$ $2n\alpha < t < 2(n+1)\alpha$ | $\frac{2}{\pi T_c}$ | 0.35 | Exponential Haar |
| $\dfrac{\alpha^2+\beta^2}{\alpha^2+\left(\beta+\dfrac{1}{T_2}\right)^2}$ | $\alpha = \sqrt{4E\beta - \beta^2}$ $\beta = \dfrac{1}{T_c^2\left(4E-\dfrac{2}{T_c}\right)}$ | $\dfrac{\alpha^2+\beta^2}{\alpha}e^{-\beta t}\sin(\alpha t)$ | $\frac{2}{\pi T_c}$ | 0.3 | Exponential Sine |
| $g_0 + \sum_{n=1}^{\infty} a_n g_n(x),\ x = \dfrac{T_c}{T_2}$ $g_n(x) = \dfrac{x^{2n-2} - x^{2n}}{(1+x^2)^{2n-1}}$ | $a_k$ computed recursively | See Appendix A | $\infty$ | $0.5 \leq m_n \leq \infty$ Variable Slope | Series Expansion |

B. Transforms on Imperfectly Polarized Data

Consider imperfectly polarized data with $$P_\tau(T_2) = 1 - e^{-\tau/T_2} \quad (6g)$$

where $$\tau = T_w/r,\ r = \left\{\frac{T_1}{T_2}\right\}$$

and $T_w$ is the wait time. This polarization factor plays an important role in saturation-recovery-CPMG pulse sequence and in enhanced precision mode (EPM) used in downhole applications. We show below that the integral transform approach that was developed on fully polarized data with $P_\tau(T_2) = 1\,\forall T_2$ can be applied to imperfectly polarized data as well. From eqns. (1) and (6g)

$$G(t) = \int_0^\infty e^{-t/T_2} f(T_2) dT_2 - \int_0^\infty e^{-(t+\tau)/T_2} f(T_2) dT_2 \quad (6h)$$

Let the fully polarized data be denoted by M(t), where $$M(t) = \int_0^\infty e^{-t/T_2} f(T_2) dT_2. \quad (6i)$$

Equation (6h) can then be cast as follows $$G(t) = M(t) - M(t+\tau) \quad (6j)$$

For a finite time t we have $$\lim_{N\to\infty} M(t+N\tau) = 0. \quad (6l)$$

Therefore $$\sum_{n=0}^{N-1} G(t+n\tau) = M(t) - M(t-N\tau) \quad (6m)$$

For a finite time t and in the limit $N\to\infty$, we get $$M(t) = \sum_{n=0}^{\infty} G(t+n\tau). \quad (6n)$$

Therefore, if $\tau$ is either known or estimated, the fully polarized data M(t) can be reconstructed using equation (6n) from the measured data G(t). Integral transforms can be applied to M(t) to directly estimate linear functionals of $f(T_2)$.

Effect of Noise

In practice we have a limited number of noisy samples of the form $$\tilde{G}(it_E) = G(it_E) + n(it_E), i = 1, \ldots, N. \quad (6o)$$

Using equation (6n) will result on a modified noise $$n_s(it_E) = \sum_{j=0}^{N} n(it_E + j\tau) \quad (6p)$$

with variance $$\sigma_M^2 = N\sigma_\epsilon^2. \quad (6q)$$

For noisy data, it may be desirable to perform a denoising procedure before applying equation (6n).

C. Transforms on Data from Logging Tools

The function k(t) can also be found using a combination of numerical and analytical methods as follows. This method is illustrated with an example in logging tools where the polarization factor $P_\tau(T_2)$ tends to be more complex and depends on a number of parameters including hardware design such as length of permanent magnet, cable speed, etc. For simplicity, we have ignored the subscript τ in the polarization term in this sub-section. In logging applications, we have found that over a range of factors, $P(T_2)$ is well represented by $$P(T_2) = \frac{1}{\sum_{k=0}^{\infty} a_k e^{-bk/T_2}} \quad (6r)$$

Equation (6r) is a good fitting function $f$ or a wide range of parameters. For example, the imperfectly polarized data in the last sub-section is obtained from equation (6r) with b=τ and $a_k = 1 \forall k$. Similarly, at a range of cable speeds, the fit from equation (6r) matches $P(T_2)$ reasonably well. The polarization factor in logging tools is a complex function of tool geometry, operational constraints such as logging speed and and pulse sequence. In a number of circumstances, at logging speeds varying from 800-2000 ft/hour, the fit (solid line) from equation (6r) fits the polarization factor very well.

The fully polarized data M(t) can be reconstructed from G(t). From eqns. (6i) and (6n), we get $$M(t) = \int_0^\infty e^{-t/T_2} f(T_2) \frac{P(T_2)}{P(T_2)} dT_2 \quad (6s)$$

$$= \int_0^\infty e^{-t/T_2} f(T_2) P(T_2) \left[ \sum_k a_k e^{-bk/T_2} \right] dT_2$$

$$= \sum_k a_k \int_0^\infty e^{-(t+bk)/T_2} P(T_2) f(T_2) dT_2$$

$$= \sum_k a_k G(t + bk).$$

Integral transforms can be applied to M(t) to directly estimate linear functionals of $f(T_2)$.

Method 2: The function k(t) can also be found numerically as follows. For example, it is possible that either $P_\tau(T_2)$ or $K(T_2)$ is not well approximated by a closed form expression or an analytical k(t) does not exist for a specified $K(T_2)$. In this case, k(t) can be computed numerically as follows. For example, consider the case where the data are fully polarized with $P_\tau(T_2) = 1 \forall T_2$. The desired $K(T_2, T_c)$ can be shown as a trace. A numerical least squares approximation to k(t, T) can be obtained using singular value decomposition (SVD), with $$\tilde{k}(t) \approx V_n \Sigma_n^{-1} U_n^T K(T_2) \quad (6t)$$

Here matrices U, Σ and V are obtained by SVD of function $e^{-t/T_2}$ and n refers to the number of significant singular values.

In another embodiment of the method, the function k(t) can be found such that its Laplace transform minimizes the error with respect to the desired $K(T_2, T_c)$ and has a minimal energy, $$\min_{k(t)} \| \int_0^\infty k(t) e^{t/T_2} dt - K(T_2, T_c) \|^2$$

such that $$\|k\|^2 < E$$

Method 3: The function k(t) can also be found using the equivalence of the convolution-multiplication operation between the time and $T_2$ domain. This is further described below. We show that the product of two functions in the $T_2$ domain corresponds to convolution in the time-domain. This property implies that the integral transforms described in this memo can also be combined in the time domain to estimate other parameters. For example, the moments of a specified region of the $T_2$ distribution can be computed by using a function computed as the convolution of the Mellin operator and the Exponential Haar transform. Consider two different integral transforms of the measured data, where function k(t) in equation (5) is represented by $k_1(t)$ and $k_2(t)$ respectively, $$A_1 = \int_0^\infty k_1(t) G(t) dt = \int_0^\infty K_1(T_2) P_\tau(T_2) f(T_2) dT_2 \quad (6u)$$

$$A_2 = \int_0^\infty k_2(t) G(t) dt = \int_0^\infty K_2(T_2) P_\tau(T_2) f(T_2) dT_2. \quad (6v)$$

Here, the functions $K_1(T_2)$ and $K_2(T_2)$ correspond to different linear functionals. Our interest is in evaluation of $A_3$, where $$A_3 = \int_0^\infty K_3(T_2) P_\tau(T_2) f(T_2) dT_2, \quad (6w)$$

and $$K_3(T_2) \equiv K_1(T_2) K_2(T_2) \quad (6x)$$

$$= \int_0^\infty k_1(\tau) e^{\frac{-\tau}{T_2}} d\tau \int_0^\infty k_2(t_2) e^{\frac{-t_2}{T_2}} dt_2 \quad (6y)$$

From equation (6)

$$\int_0^\infty k_3(t) e^{-t/T_2} dt = \int_0^\infty \int_0^\infty k_1(\tau) k_2(t_2) e^{\frac{-(\tau+t_2)}{T_2}} d\tau dt_2 \quad (6z)$$

Let $\tau + t_2 = t$. Thus $$\int_0^\infty k_3(t) e^{-t/T_2} dt = \int_0^\infty \left[ \int_0^t k_1(\tau) k_2(t-\tau) d\tau \right] e^{-t/T_2} dt \quad (6aa)$$

Thus, the parameter $A_3$ can be computed as, $$A_3 = \int_0^\infty k_3(t)G(t)dt \qquad (6bb)$$

where $k_3(t)$ is obtained as a convolution of $k_1(t)$ and $k_2(t)$, $$k_3(t) = \int_0^t k_1(\tau)k_2(t-\tau)d\tau. \qquad (6cc)$$

Hence, the product of two functions in the $T_2$ domain corresponds to convolution in the time-domain. This property implies that the integral transforms described in this manuscript can also be combined to estimate other parameters. For example, this property implies that the moments of a specified region of the $T_2$ distribution can be computed by integral transforms of the measured data, using a function obtained as a convolution of the Mellin operator and the Exponential Haar transform.

Method 4: We describe below a method for computing $k(t)$ using method of successive approximations. We illustrate this with an example. Consider $K(T_2)$ is an arbitrarily sharp transition in the $T_2$ domain. Let $$x = \frac{T_c}{T_2}.$$

Let the Heaviside function $H(x)$ be defined as follows.

$$H(x) = 1 \text{ for } x < 1 \qquad (6ee)$$
$$= 0.5 \text{ for } x = 1 \qquad (6ff)$$
$$= 0 \text{ otherwise.} \qquad (6gg)$$

In this method, we define $g_0(x)$ to be a generating function if it is monotonic and takes values between 0 and 1 and satisfies the following property, $$g_0(x) + g_0\left(\frac{1}{x}\right) = 1.$$

Examples of generating functions that resemble a Heaviside function and satisfy the above property are $$g_0(x) = \frac{2}{\pi}\operatorname{atan}\left(\frac{1}{x}\right) \text{ and } g_0(x) = \frac{1}{1+x^2}$$

We seek a series of coefficients $a_n$ and functions $g(x)$, $n=1, \ldots, \infty$ such that $$H(x) = g_0(x) + \sum_{n=1}^\infty a_n g_n(x) \qquad (6ii)$$

For $n \geq 1$, we seek functions $g_n(x)$ such that the functions satisfy the following properties:

1. $g_n(x)$ should have unique inverse Laplace transform in closed-form and should exist for all x.
2. $g_n(x)$ should be anti-symmetric in log–x, with $$g_n(x) = -g_n\left(\frac{1}{x}\right). \qquad (6jj)$$

3. When x is small, $g_n(x)$: $x^n$.
4. When x is large, $g_n(x)$: $x^{-n}$.

Properties (1), (3) and (4) are self-explanatory. Property (2) follows from the Heaviside function $H(x)$ and generating function $g_0(x)$ satisfying eq. (6hh). At the first iteration, the approximate Heaviside function is $$H_1(x) = g_0(x) + a_1 g_1(x) \qquad (6kk)$$

Therefore, $$H_1\left(\frac{1}{x}\right) = g_0\left(\frac{1}{x}\right) + a_1 g_1\left(\frac{1}{x}\right) \qquad (6ll)$$

From our construction, $H_1(x)$ and $g_0(x)$ satisfy eq. (6hh). Therefore, $$1 - H_1(x) = 1 - g_0(x) + a_1 g_1\left(\frac{1}{x}\right) \qquad (6mm)$$

Thus, from equations (6kk) and (6mm), we have $$g_1(x) = -g_1\left(\frac{1}{x}\right) \cdot A$$

similar proof follows for any $g_n(x)$, $n \geq 1$.

Case 1:

$$\text{Let } g_0(x) = \frac{2}{\pi}\operatorname{atan}\left(\frac{1}{x}\right).$$

Its Taylor-series expansion is $$\frac{2}{\pi}\operatorname{atan}\left(\frac{1}{x}\right) = H(x) - \frac{2}{\pi}\left[x - \frac{x^3}{3} + \frac{x^5}{5} \ldots \right] \text{ for } ||<1. \qquad (6nn)$$

If we subtract from $g_0(x)$ the terms in the Taylor-series proportional to $x^n (n \geq 1)$, written as a function of $g_n(x)$, then, we will obtain a function that converges to 1 for $|x|<1$ and converges to 0 for $|x|>1$. Since the Taylor-series expansion has only odd-powers of x, we consider $$g_n(x) = \frac{-x^{2n-1} + x^{2n+1}}{(1+x^2)^{2n}} \qquad (6oo)$$

These functions satisfy properties (1)-(4). In addition, $$\sum_{k=1}^{\infty} a_k g_k(x) = \sum_{k=1}^{\infty} a_k \frac{-x^{2k-1} + x^{2k+1}}{(1+x^2)^{2k}} \qquad (6pp)$$

Using the series expansion for $$\frac{1}{(1+x^2)^{2k}}$$

around x=0, we get $$\sum_{k=1}^{\infty} a_k g_k(x) = \sum_{k=1}^{\infty} a_k (x^{2k+1} - x^{2k-1}) \left[ \sum_{m=0}^{\infty} (-1)^m \binom{2k+m-1}{m} x^{2m} \right] \qquad (6qq)$$

Matching the coefficients for $x^{2n-1}$ in eqns. (43) and (46) yields $$a_n = \frac{(-1)^{n-1}}{2n-1} + \sum_{k=1}^{n-1} (-1)^{n-k} a_k \left[ \binom{n+k-2}{n-k-1} + \binom{n+k-1}{n-k} \right]. \qquad (6rr)$$

The first three coefficients are $$a_1 = \frac{2}{\pi}, \; a_2 = \frac{8}{3} a_1 \text{ and } a_3 = \frac{128}{15} a_1. \text{ Let } \tau = \frac{t}{T_c}.$$

The inverse Laplace transforms of the first three terms in the series expansion are $$L^{-1}\left[\frac{x-x^3}{(1+x^2)^2}\right] = \frac{1}{T_c}[\tau\sin(\tau) - \cos(\tau)]$$

$$L^{-1}\left[\frac{x^3-x^5}{(1+x^2)^4}\right] = \frac{1}{T_c}\left[\frac{1}{24}(-6\tau^2\cos(\tau) - 6\tau\sin(\tau) + \tau^3\sin(\tau))\right]$$

$$L^{-1}\left[\frac{x^5-x^7}{(1+x^2)^6}\right] =$$
$$\frac{1}{T_c}\left[\frac{1}{1920}(30\tau^2\cos(\tau) - 15\tau^4\cos(\tau) - 30\tau\sin(\tau) - 55\tau^3\sin(\tau) + \tau^5\sin(\tau))\right].$$

A general expression for the inverse Laplace transform for $g_n(x)$ can be obtained from the following:

$$L^{-1}\left[\frac{x^r - x^{r+2}}{(1+x^2)^{r+1}}\right] = \qquad (6ss)$$

$$\frac{\tau^{r-1}}{T_c \Gamma(r)\Gamma(r+2)} \left[ \tau^2 \Gamma(r) \,_1F_2\left(r+1; \frac{r}{2}+1, \frac{r}{2}+\frac{3}{2}; -\frac{\tau^2}{4}\right) - \Gamma(r+2) \,_1F_2\left(r+1; \frac{r}{2}+\frac{1}{2}, \frac{r}{2}; -\frac{\tau^2}{4}\right) \right]$$

where $_1F_2$ refers to the generalized hypergeometric function.

Case 2:

Let $g_0(x) = \frac{1}{1+x^2}$.

Its Taylor-series expansion (around x=0) is $$\frac{1}{1+x^2} = H(x) - x^2 + x^4 - x^6 \ldots \qquad (6tt)$$

Since the series expansion has only even powers of x, we consider $g_n(x)$ of the form, $$g_n(x) = \frac{x^{2n-2} - x^{2n}}{(1+x^2)^{2n-1}}, n = 1, 2, \ldots \qquad (6uu)$$

These functions satisfy properties (1)-(4). Using series expansion of $$\frac{1}{(1+x^2)^{2n-1}}$$

around x=0, we get, $$\sum_{k=1}^{\infty} a_k g_k(x) = \sum_{k=1}^{\infty} a_k \frac{-x^{2k-2} + x^{2k}}{(1+x^2)^{2k-1}} = \qquad (6vv)$$

$$\sum_{k=1}^{\infty} a_k (x^{2k-2} - x^{2k}) \left[ \sum_{m=0}^{\infty} (-1)^m \binom{2k+m-2}{m} x^{2m} \right] \qquad (6ww)$$

Matching the coefficients for $x^{2n-2}$ in eqns. (49) and (52) yields $$a_n = (-1)^{n-1} - \sum_{k=1}^{n-1} (-1)^{n-k} a_k \left[ \binom{n+k-2}{n-k} + \binom{n+k-3}{n-k-1} \right]. \qquad (6xx)$$

The first three coefficients are $a_1=0$, $a_2=-1$ and $a_3=-3$. Let $$\tau = \frac{t}{T_c}.$$

The inverse Laplace transforms of the first three terms in the series expansion are $$L^{-1}\left[\frac{1-x^2}{(1+x^2)}\right] = \frac{1}{T_c}[2\sin(\tau) - \delta(\tau)]$$

$$L^{-1}\left[\frac{x^2-x^4}{(1+x^2)^3}\right] = \frac{1}{T_c}\left[\frac{1}{4}(\tau^2\sin(\tau) - \sin(\tau) - 3\tau\cos(\tau))\right]$$

-continued $$L^{-1}\left[\frac{x^4 - x^6}{(1+x^2)^5}\right] =$$

$$\frac{1}{T_c}\left[\frac{1}{192}(\tau^4 \sin(\tau) - 10\tau^3 \cos(\tau) - 21\tau^2 \sin(t) - 3\sin(\tau) + 3\tau\cos(\tau))\right].$$

It can be shown that the Taylor-series expansion of the generating function in terms of anti-symmetric higher-order polynomials systematically leads to convergence of the generating function to a Heaviside function in log(x) space.

As explained in previously incorporated U.S. Ser. No. 13/333,232, the above describes methods for computing linear functionals of the distribution function without first computing the distribution of relaxation times. These methods involve a linear transform of the measured data using integral transforms. Different linear functionals of the distribution function can be obtained by choosing appropriate functions in the integral transforms. This approach can be used such that integral transforms can be computed on data corresponding to longitudinal relaxation time ($T_1$), and such that integral transforms can be computed on data corresponding to diffusion coefficient (D). In addition, this approach can be extended to multiple dimensions.

Using the techniques given in previously incorporated U.S. Ser. No. 13/333,232, it is possible to estimate the uncertainty in the parameters. Let the discretized version of the linear transform be denoted by $A=k^T G$, where k is the discretization of the k(t) in equation (4) and G refers to the discretization of the measured data indications. Let $\sigma_\epsilon^2$ be the variance of the vector of measurement indications G. Then the variance of A is given by $$\sigma_A^2 = \sigma_\epsilon^2 \|k\|^2 \qquad (7)$$

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

Embodiments are provided for the estimation of an NMR-related distribution that is consistent with NMR measurements and uses linear functionals directly estimated from the measurement indications by integral transforms as constraints in a cost function. This cost function includes indications of the measurement data, Laplace transform elements and the constraints, and an NMR-related distribution estimation is made by minimizing the cost function. The NMR-related distribution estimation may then be used to find parameters of the sample. Where the sample is a rock or a formation, the parameters may include parameters such as rock permeability and/or hydrocarbon viscosity, bound and free fluid volumes, among others. The parameters may then be used, if desired, in models, equations, or otherwise to act on the sample, such as in recovering hydrocarbons from the formation. Examples of NMR-related distributions include transverse relaxation time ($T_2$) distributions, longitudinal relaxation time ($T_1$) distributions, Diffusion (D) distributions, and various multi-dimensional distributions, although embodiments are not limited thereto.

BRIEF DESCRIPTION OF THE DRAWINGS

FIGS. 3a-3d provide sets of graphs, each set providing a model of simulated $T_2$ distributions and noise-free echoes used in benchmarking ILT processing and the processing of an embodiment on simulated data.

FIGS. 5a-5b show sets of histograms comparing estimates at different signal to noise ratios obtained by ILT processing and the processing of an embodiment for the model of FIG. 3a.

DETAILED DESCRIPTION OF THE EMBODIMENTS

In one embodiment, constraints obtained using the integral transform approach described previously incorporated U.S. Ser. No. 13/333,232 are applied to a cost function which also includes indications of measured NMR data and Laplace transform elements, and a $T_2$ distribution estimation is made by minimizing the cost function. The $T_2$ distribution estimation may then be used to find parameters of the sample.

Figure 1:
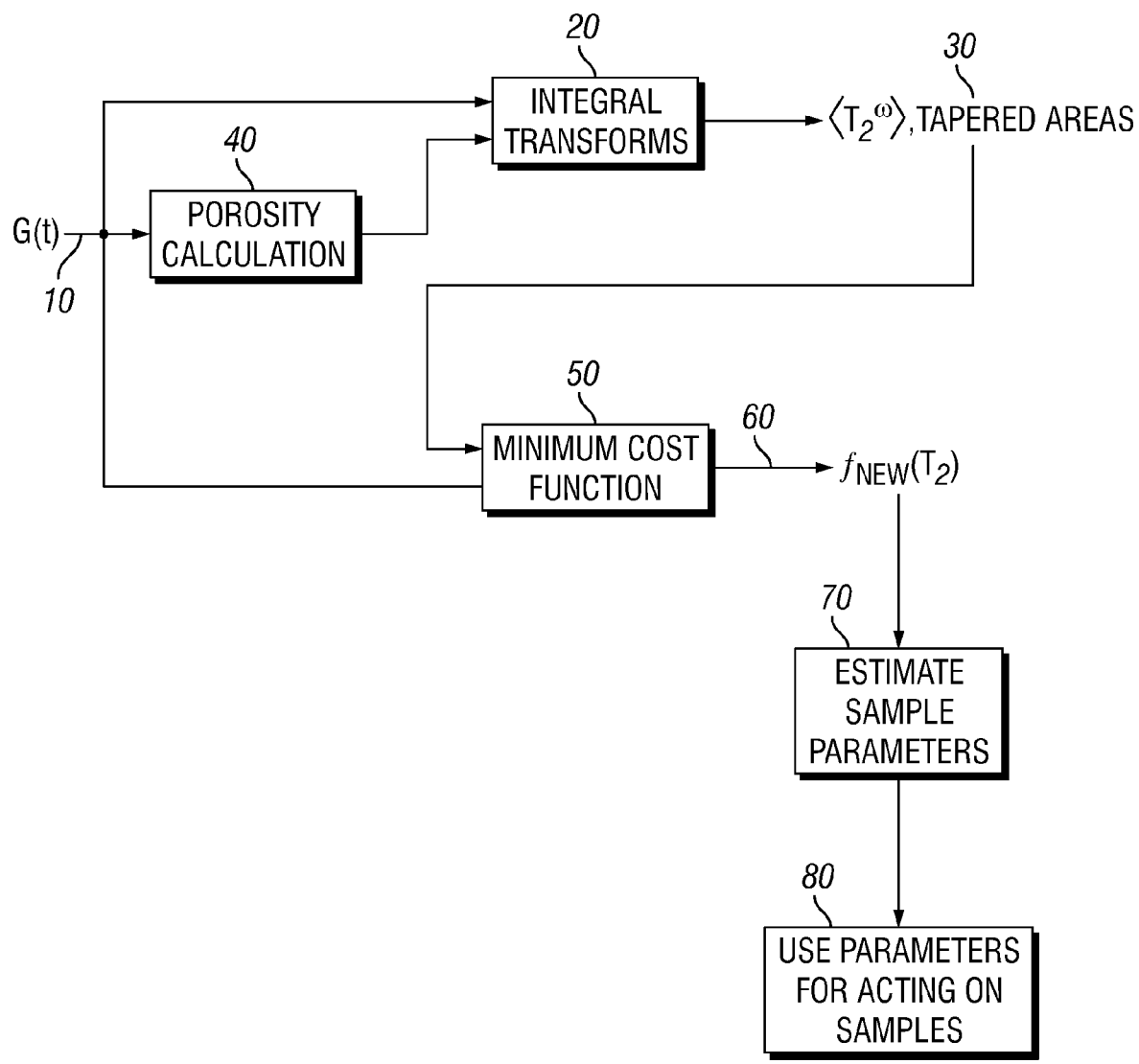
FIG. 1 is a high level block diagram showing a method of an embodiment.

In an embodiment seen in FIG. 1, data G(t) 10, indicative of what might have been measured by an NMR tool as a result of having applied a pulse sequence to a sample, is processed at 20 using the integral transform approach described previously incorporated U.S. Ser. No. 13/333,232 to provide a plurality of linear functionals, e.g., $\langle T_2^\omega \rangle$, Tapered areas 30. As indicated, porosity calculations 40 which may be obtained by processing the NMR data G(t), or from other sources can be used as inputs to the integral transform approach processing 20. The linear functionals obtained at 30 are then used as constraints or "priors" in a cost function 50 incorporating them as well as Laplace transform elements and utilizing indications of the NMR data in order to generate a $T_2$ distribution denoted by $f_{NEW}(T_2)$ 60. The calculated $T_2$ distribution 60 is an answer product that itself may be used for any of many purposes. By way of example only, the $T_2$ distribution 60 may be used at 70 to generate an estimate of one or more parameters or properties of the sample. Where the sample is a rock or a formation, the parameters may include parameters such as rock permeability and/or hydrocarbon viscosity, bound and free fluid volumes, among others. The parameters may then be used at 80, if desired, in models, equations, or otherwise to act on the sample, such as in recovering hydrocarbons from the formation.

It should be appreciated that the data acquired at the NMR tool can result from any of a variety of pulse sequences including, but not limited to CPMG, diffusion editing, inversion-recovery, saturation-recovery, and enhanced precision mode (EPM) where the data are acquired at two different wait times.

According to an embodiment, the linear constraints generated by using the integral transform approach can be included into the problem formulation in a number of ways. While one example is described below with constraints from moments and areas being included in the problem formulation, the problem may be formulated with other constraints.

Constraints from the moments and areas determined using the integral transform approach described previously incorporated U.S. Ser. No. 13/333,232 can be included in the problem formulation as follows. Let G be a vector containing indications of the NMR measurements made by an NMR tool on a sample (e.g., the data itself, the data in compressed form by means of the singular value decomposition or windows sum, or other indications of the data), and let L be a matrix representing the discretization of the function in equation (1). Assume that $N_m$ moments denoted by $\langle T_2^{\omega_i} \rangle$, i=1, . . . , $N_m$, and $N_a$ areas denoted by $B_i$, i=1, . . . , $N_a$ are estimated directly by means of the appropriate integral transforms on G(t) as described in previously incorporated Ser. No. 13/333,232. A cost function with respect to $f_{NEW\,T2}f_{NEW}(T_2)$ may be minimized, $$\min_{f_{NEW} \geq 0} \|W(\overline{G} - \overline{L}f_{NEW})\|^2 + \alpha \|f_{NEW}\|^2 \quad (8)$$

where $f_{NEW}$ is a discretized vector version of an underlying density function $f_{NEW}(T_2)$, W, as described in more detail below, is a covariance matrix of uncertainties in the parameters, α is a regularization parameter, $$\overline{G} = \begin{bmatrix} G \\ \langle T_2^{\omega_1} \rangle \\ \vdots \\ \langle T_2^{\omega_{N_m}} \rangle \\ B_1 \\ \vdots \\ B_{N_a} \end{bmatrix} \quad (9)$$

is an extended vector containing the indications of the measurements G as well as the constraints (moments $\langle T_2^{\omega_i} \rangle$ and areas $B_i$) generated by the integral transform approach, and $\overline{L}$ is the extended matrix, $$\overline{L} = \begin{bmatrix} L \\ \frac{1}{\phi} T_{2,min}^{\omega_1} & \cdots & \frac{1}{\phi} T_{2,max}^{\omega_1} \\ & \ddots & \\ \frac{1}{\phi} T_{2,min}^{\omega_{N_m}} & \cdots & \frac{1}{\phi} T_{2,max}^{\omega_{N_m}} \\ H(T_{c_1}, T_2) \\ \vdots \\ H(T_{N_a}, T_2) \end{bmatrix} \quad (10)$$

where L is a Laplace transform matrix with components $(L)_{ij} = P_\tau(T_{2,j})e^{-t_i/T_{2,j}}$, φ is the porosity, $H(T_c, T_2)$ represent the tapered Heaviside function varying smoothly between 0 and 1 with $H(T_c, T_2) = 0.5$ when $T_2 = T_c$ as described in previously incorporated U.S. Ser. No. 13/333,232, and $T_{2,min}$ and $T_{2,max}$ represent the minimum and maximum value of the discretized $T_2$ vector so that for a given $T_2$ distribution $f_{NEW}$ with components $f_{NEW}(T_{2,i})$ the ω-th moment is defined as $$\langle T_2^\omega \rangle = \frac{1}{\phi} \sum_{i=min}^{max} T_{2,i}^\omega f_{NEW}(T_{2,i}) \quad (11)$$

Thus, $\overline{L}$ contains Laplace transform elements as well as functions of the constraints. As previously mentioned, W is the co-variance matrix of uncertainties in the parameters and may be described by $$W = \begin{bmatrix} \frac{1}{\sigma_\epsilon} & & & & & \\ & \frac{1}{\sigma_{\omega_1}} & & & & \\ & & \ddots & & & \\ & & & \frac{1}{\sigma_{\omega_{N_m}}} & & \\ & & & & \frac{1}{\sigma_{B_i}} & \\ & & & & & \ddots \\ & & & & & & \frac{1}{\sigma_{N_m}} \end{bmatrix} \quad (12)$$

where $\sigma_\epsilon$ is the standard deviation of noise in the measurements and $\sigma_{\omega_i}$ and $\sigma_{B_i}$ are the estimated uncertainties in the moments and areas estimated according to equation (7).

It will be appreciated by those skilled in the art that any of many optimization routines may be utilized to solve the cost function of equation (8) for $f_{NEW}$. By way of example only, MatLab® software sold by MathWorks of Natick, Mass. includes a NNLS (non-negative least squares) routine which may be used to solve equation (8). Likewise, by way of example only, IMSL (International Mathematics and Statistics Library) sold by Rogue Wave Software of Boulder Colorado includes optimization routines which may be used to solve equation (8).

Figure 2:
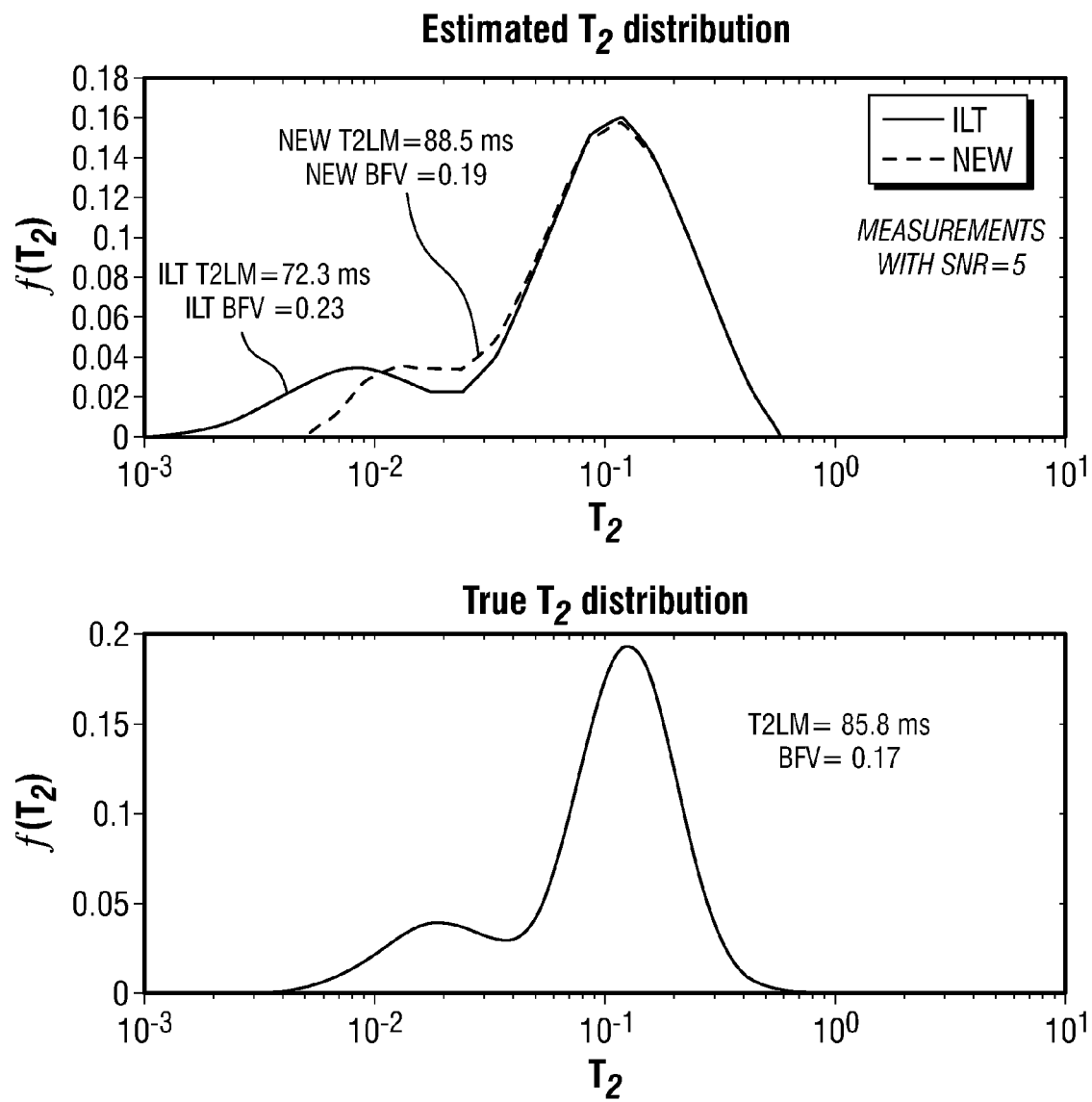
FIG. 2 provides a first graph of an assumed $T_2$ distribution and a second graph comparing estimated $T_2$ distributions resulting from ILT processing and processing of an embodiment.
Figures 3A, 3B:
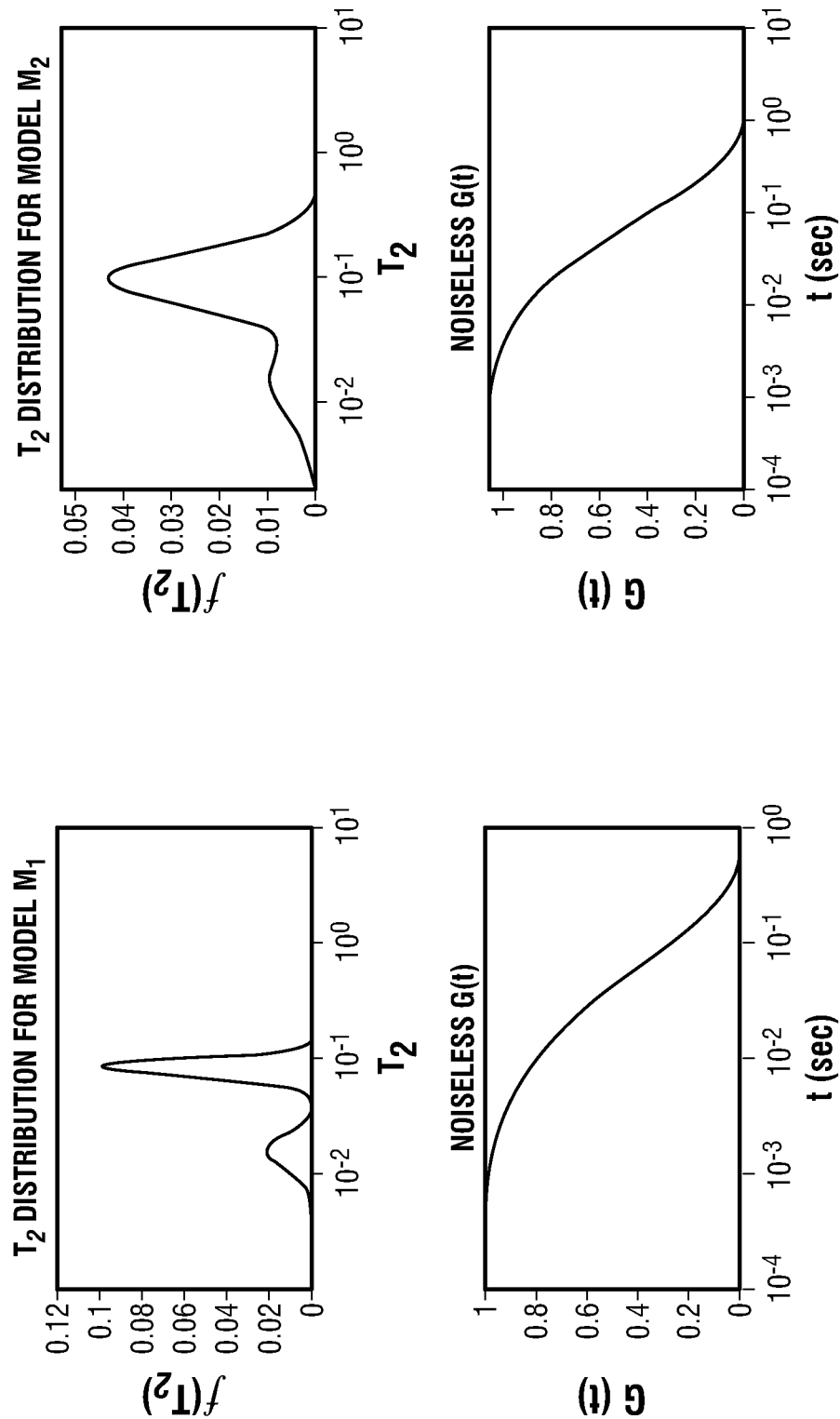

Extensive testing with simulated data shows that the addition of constraints generated by the integral transform approach as part of the data processing tends to eliminate artifacts in the estimated $T_2$ distribution. For example, the bottom graph of FIG. 2 shows an actual $T_2$ distribution, and the top graph of FIG. 2 compares estimated $T_2$ distributions using the standard ILT processing and the processing of the described embodiment (denoted "NEW" in the Figures) for one noisy data set with a noise standard deviation $\sigma_\epsilon = 0.2$. The general shape of the distribution using the embodiment appears a little closer than the distribution using standard ILT processing to the general shape of the actual distribution. In addition, parameters such as the mean-log of the $T_2$ distribution referred to as T2LM, and the bound fluid volume (BFV) obtained with a sharp cut-off of 33 msec from ILT are considerably closer to the true values for the embodiment (true T2LM=85.8 ms, ILT T2LM=72.3 ms, NEW T2LM=88.5 ms; true BFV=0.17, ILT BFV=0.23, NEW BFV=0.19). For both ILT and the embodiment a nominal value of α=1 was chosen.

An embodiment was benchmarked on simulated data obtained from $T_2$ distributions for four models $M_1$-$M_4$ shown respectively in FIGS. 3a-3d. Data are generated assuming a fixed porosity of φ=1 with additive white Gaussian noise with standard deviation per echo of $\sigma_\epsilon = 0.2$ (signal-to-noise ratio SNR=50) and $\sigma_\epsilon = 0.2$ (SNR=5) representing lab (i.e., core) data and log data, respectively. To demonstrate the performance of the algorithm on fully and partially polarized data, it is assumed that data from models $M_1$ and $M_2$ are fully polarized. Data from models $M_3$ and $M_4$ are obtained in the EPM mode at two different wait times, indicated in the FIGS. 3c and 3d by the legend—'main pulse' and 'burst'.

Figure 4:
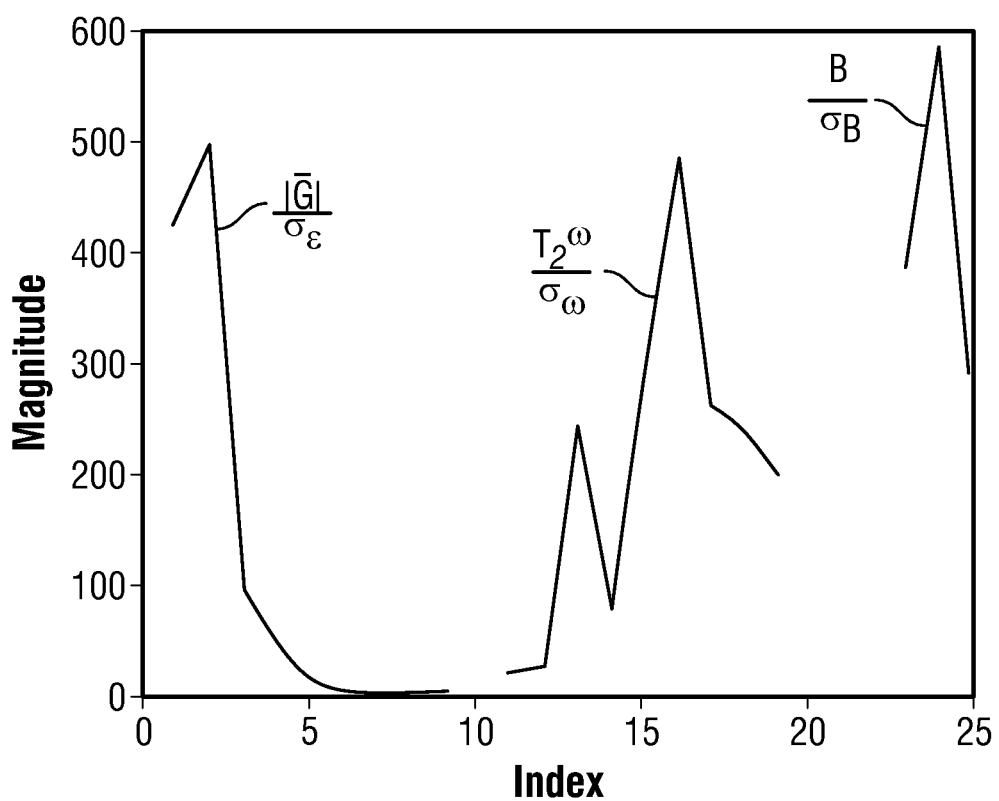
FIG. 4 is a graph showing values of weighted terms used in the processing of an embodiment.

The noisy data are analyzed using the ILT processing and the embodiment. For each realization, the same regularization parameter α was used in ILT and embodiment. The value of α was selected according to the Butler-Reed-Dawson algorithm. See "J. P. Butler, et al., "Estimating solutions of the first kind integral equations with nonnegative constraints and optimal smoothing, *SIAM J. Numerical Analysis*, 18(3):381-397, 1981. Several moments and areas in equation (8) were tested initially but in the following simulations twelve moments with ω between −0.5 and 1 and three tapered areas with $T_c$=0.01, 0.1 and 1 sec. are considered. The algorithm is not sensitive to the number of moments and areas. The data was compressed using the truncated singular value decomposition and the number of singular values was selected to achieve a condition number (ratio between first singular value and last singular value used in the calculations) of 1000. FIG. 4 shows the weighted and compressed data (first 10 values), moments (next 12 values), and areas (last 3 values) used in equation (8).

Figure 5A:
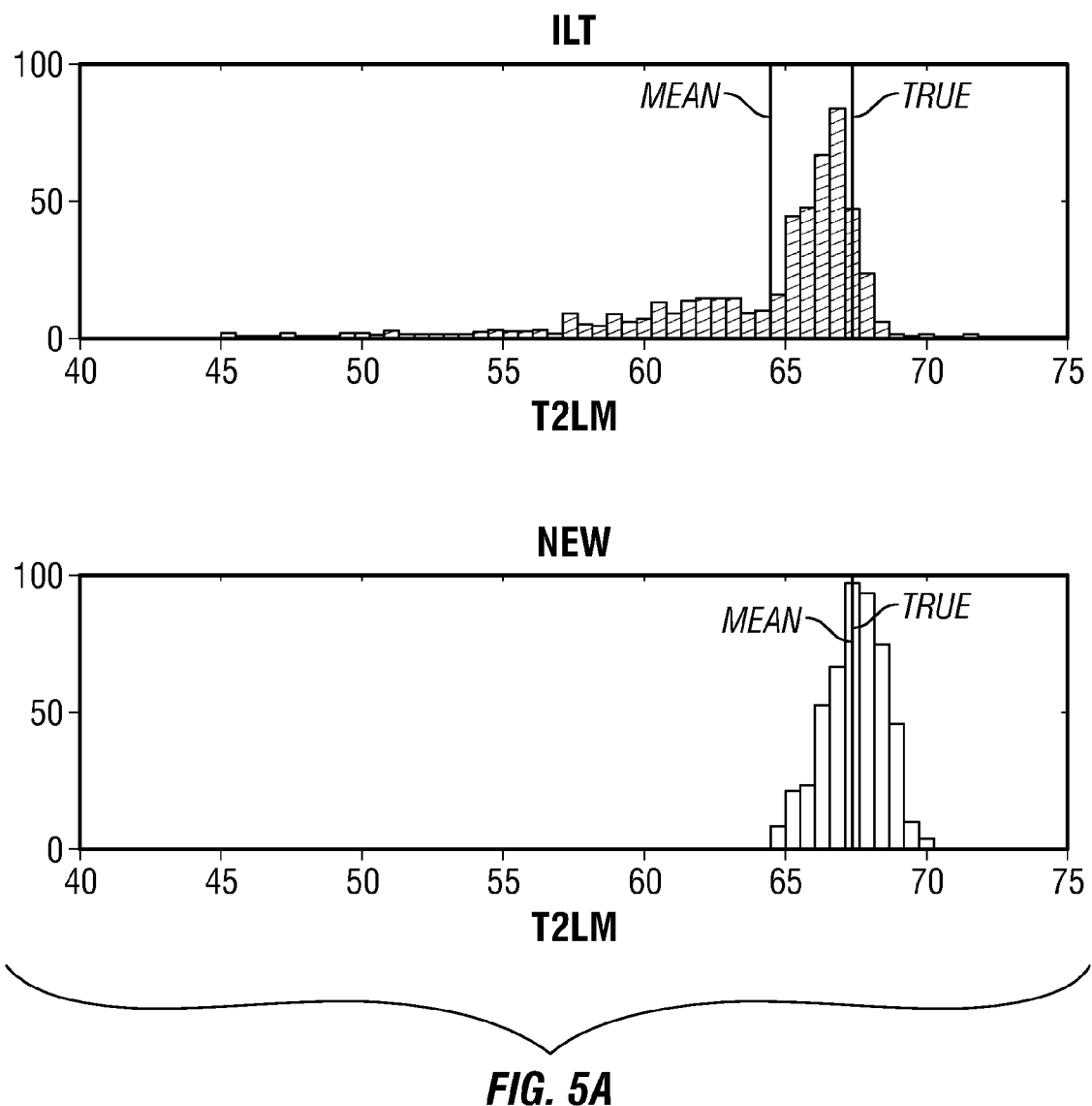
Figure 5B:
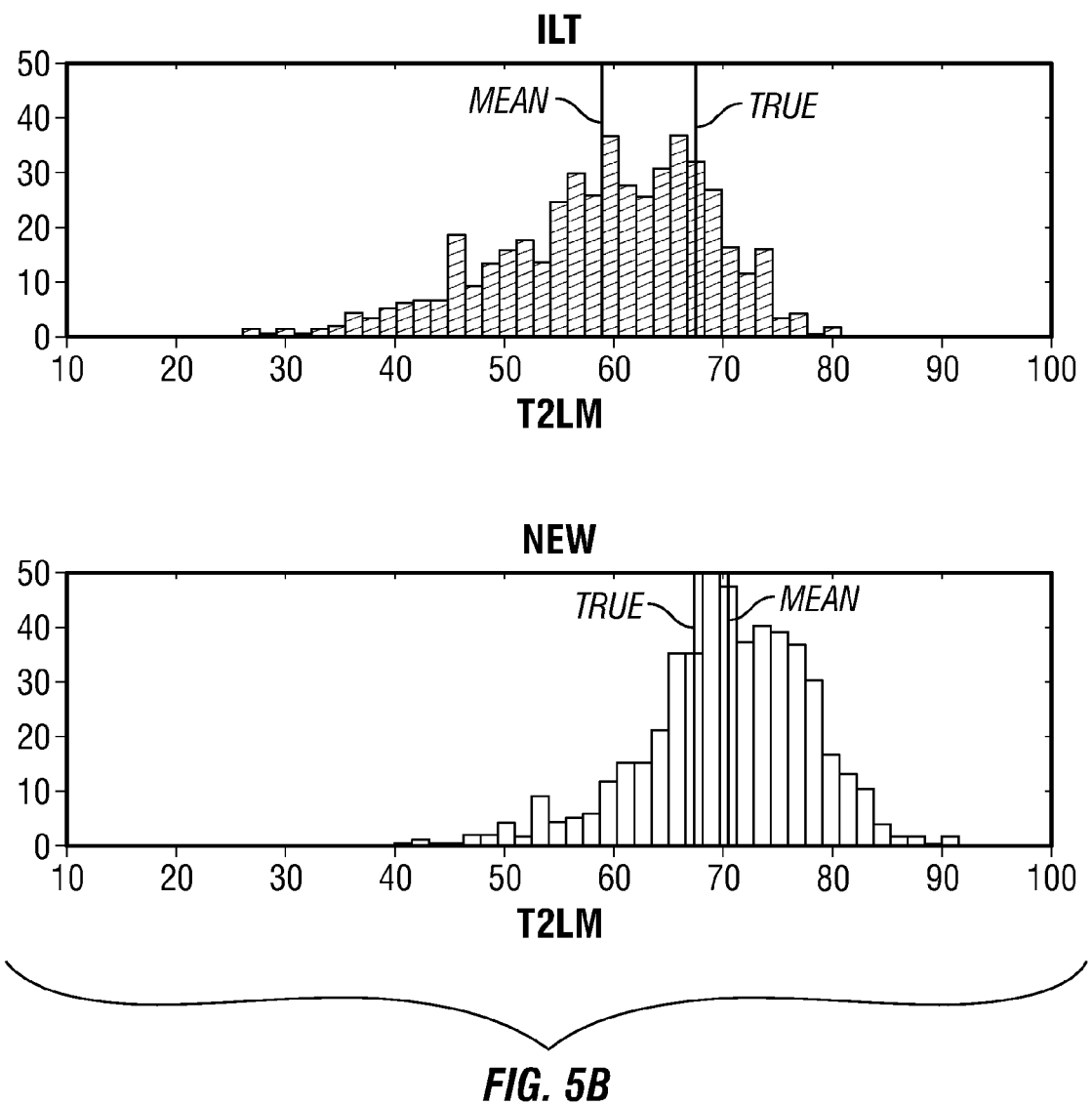
Figure 6A:
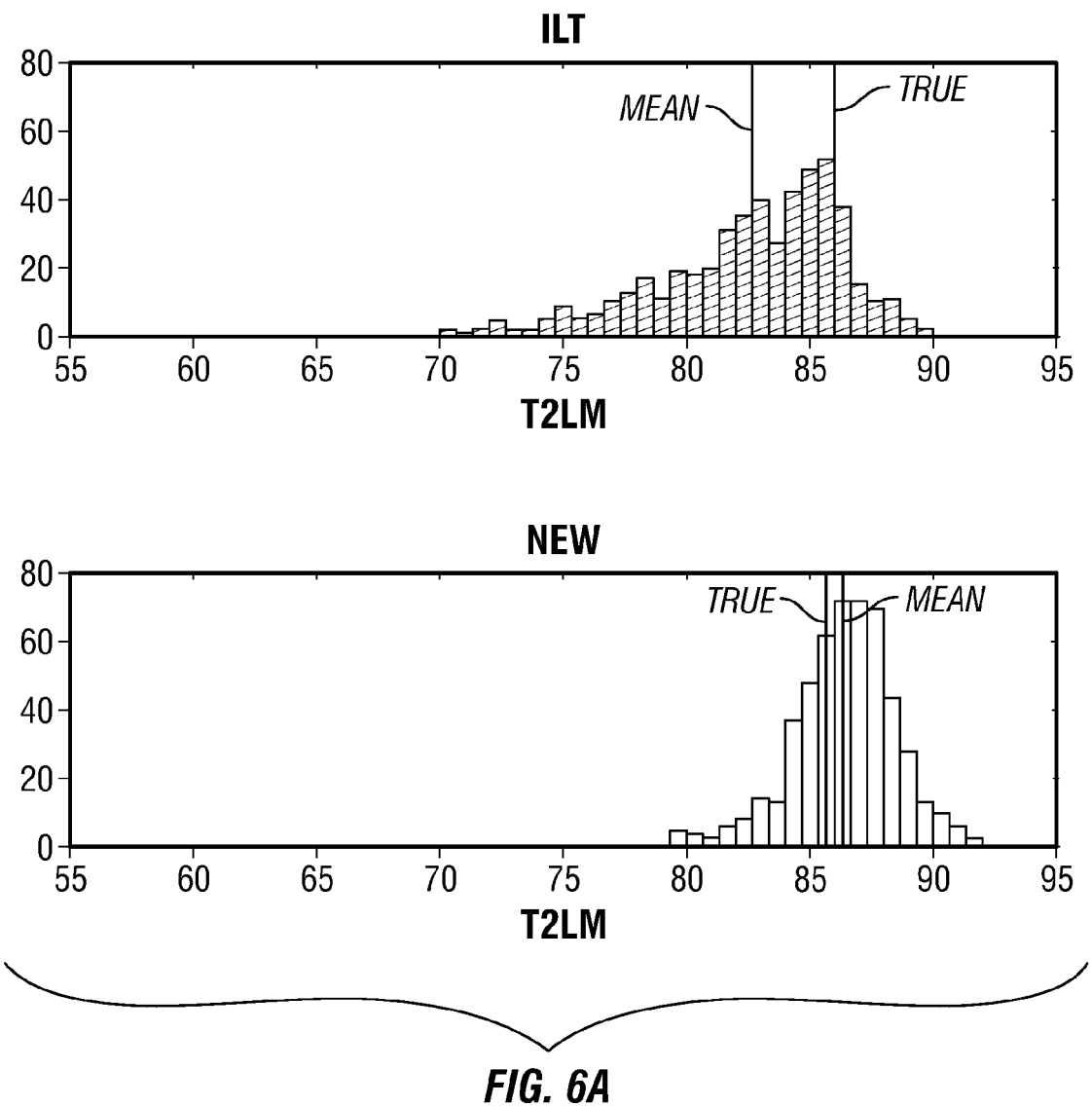
FIGS. 6a-6b show sets of histograms comparing estimates at different signal to noise ratios obtained by ILT processing and the processing of an embodiment for the model of FIG. 3b.
Figure 6B:
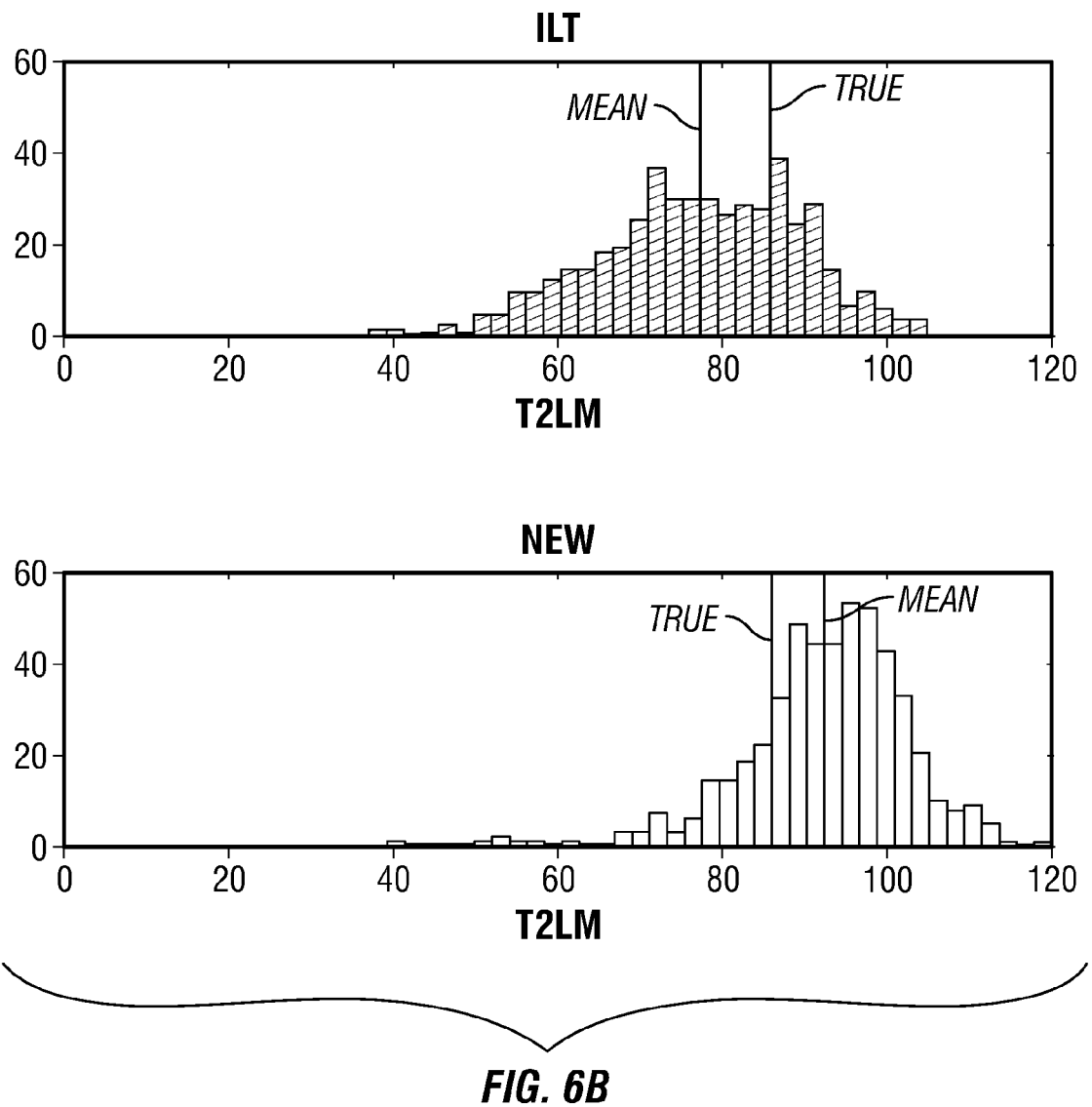

As before, two parameters, T2LM and BFV, are used to compare the performance of ILT and the embodiment. FIGS. 5a and 5b respectively show the estimated T2LM for Model $M_1$ with SNR=50 and SNR=5 analyzed with 500 realizations of noise. As seen in FIGS. 5a and 5b, the embodiment (NEW) estimates show a smaller bias and standard deviation in the estimated T2LM than do the ILT estimates. This behavior was also seen for the other models (see, for example, FIGS. 6a and 6b which compare the performance of ILT and embodiment for Model $M_2$). The performance of ILT and the embodiment for estimating T2LM and BFV are also summarized in Tables 1a, 1b, 2a, and 2b where μ indicates the mean of the estimate, σ indicates the standard deviation, $\hat{\sigma}$ represents the estimated uncertainty, and rmse is the root mean square error defined for any estimate Est as $$rmse \sqrt{\langle (\text{Est}-\text{Truevalue})^2 \rangle}$$

where $\langle \cdot \rangle$ represents the mean, and nmrse represents the normalized rmse defined as $$nrmse = \frac{rmse}{\text{True Value}} \times 100 \qquad 1$$

TABLE 1a

Comparison of T2LM; SNR = 50

| Models | True T2LM (ms) | ILT μ ± σ | ILT nrmse (%) | NEW μ ± σ | NEW nrmse (%) | $\hat{\sigma}_{T2LM}$ μ |
|---|---|---|---|---|---|---|
| $M_1$ | 67.2 | 64.4 ± 3.6 | 6.8 | 67.3 ± 1.1 | 1.7 | 2.1 |
| $M_2$ | 85.8 | 82.7 ± 3.8 | 5.7 | 86.4 ± 2.1 | 2.5 | 3 |
| $M_3$ | 54.8 | 54.1 ± 0.9 | 2 | 54.6 ± 0.3 | 0.6 | 0.4 |
| $M_4$ | 73.8 | 73.1 ± 1.3 | 1.9 | 73.8 ± 0.5 | 0.6 | 0.5 |

TABLE 1b

Comparison of T2LM; SNR = 5

| Models | True | ILT μ ± σ | ILT nrmse (%) | NEW μ ± σ | NEW nrmse (%) | $\hat{\sigma}_{T2LM}$ μ |
|---|---|---|---|---|---|---|
| $M_1$ | 67.2 | 58.7 ± 10.6 | 20.2 | 70.2 ± 8.1 | 12.8 | 16.1 |
| $M_2$ | 85.8 | 77.2 ± 13 | 18.2 | 92.8 ± 9.8 | 14 | 21 |

TABLE 1b-continued

Comparison of T2LM; SNR = 5

| Models | True | ILT μ ± σ | ILT nrmse (%) | NEW μ ± σ | NEW nrmse (%) | $\hat{\sigma}_{T2LM}$ μ |
|---|---|---|---|---|---|---|
| $M_3$ | 54.8 | 50.3 ± 6.1 | 13.8 | 53.3 ± 2.3 | 5 | 2.9 |
| $M_4$ | 73.8 | 69 ± 6.2 | 10.7 | 71.5 ± 3.2 | 5.3 | 4.1 |

TABLE 2a

Comparison of BFV; SNR = 50

| Models | True | ILT μ ± σ | ILT rmse | NEW μ ± σ | NEW rmse |
|---|---|---|---|---|---|
| $M_1$ | 0.28 | 0.25 ± 0.019 | 0.03 | 0.25 ± 0.013 | 0.03 |
| $M_2$ | 0.17 | .014 ± 0.012 | 0.03 | 0.13 ± 0.009 | 0.04 |
| $M_3$ | 0 | 0 ± 0.003 | 0 | 0 ± 0.001 | 0 |
| $M_4$ | 0 | 0 ± 0.003 | 0 | 0 ± 0 | 0 |

TABLE 2b

Comparison of BFV; SNR = 5

| Models | True | ILT μ ± σ | ILT rmse | NEW μ ± σ | NEW rmse |
|---|---|---|---|---|---|
| $M_1$ | 0.28 | 0.22 ± 0.07 | 0.03 | 0.16 ± 0.066 | 0.14 |
| $M_2$ | 0.17 | 0.17 ± 0.058 | 0.03 | 0.1 ± 0.055 | 0.09 |
| $M_3$ | 0 | 0.14 ± 0.066 | 0 | 0.09 ± 0.06 | 0.11 |
| $M_4$ | 0 | 0.11 ± 0.043 | 0 | 0.06 ± 0.04 | 0.07 |

These tables show that the estimates of the T2LM from the embodiment (NEW) have less bias and either smaller or comparable variance than the ILT processing. The results were mixed for estimation of BFV, especially in the case of low SNR. The tables also indicate that the uncertainty estimate of parameters such as T2LM compares reasonably well with the standard deviation as obtained from Monte-Carlo simulations of the data.

Figure 7:
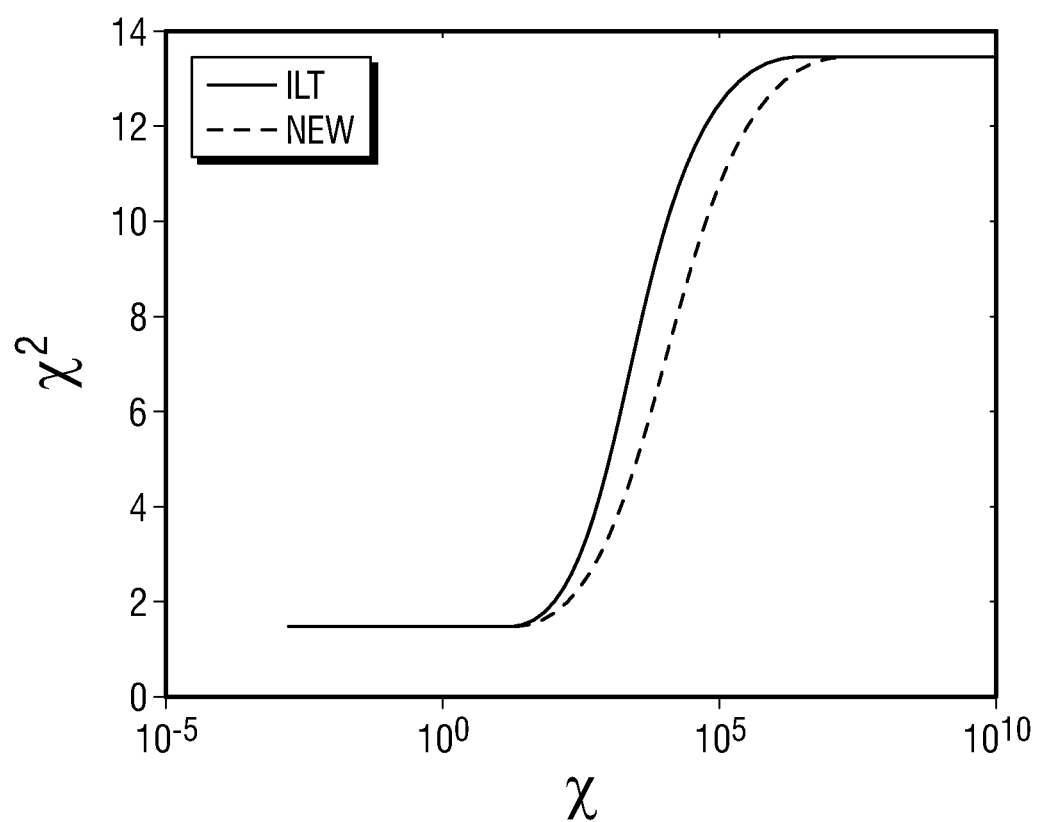
FIG. 7 is a graph showing the fit error as a function of a parameter for the model of FIG. 3a for the ILT processing and for the processing of an embodiment at a given signal to noise ratio.

It was found that the addition of linear functionals as constraints to the estimation of the $T_2$ distribution reduces the dependence of the error in the fit to the regularization parameter. Let $\chi_{ILT}^2 = \|G - Kf_{ILT}\|^2$ be the error in the fit obtained from using the $T_2$ distribution $f_{ILT}$ estimated by using ILT and $\chi_{NEW}^2 = \|G - Kf_{NEW}\|^2$ the corresponding error in the fit using the embodiment. FIG. 7 shows the fit error as a function of α from each. In this example, the data is obtained from model $M_1$ with SNR=5. It is observed that the fit error is independent of α for a larger range when using the embodiment.

According to another embodiment, instead of minimizing a cost function with respect to a transverse relaxation time ($T_2$) to obtain a $T_2$ distribution estimation $f(T_2)$, a cost function is minimized with respect to a longitudinal relaxation time ($T_1$) to obtain a $T_1$ distribution estimation $f(T_1)$. More specifically, as in FIG. 1, data G(t) indicative of what might have been measured by an NMR tool as a result of having applied a pulse sequence to a sample, is processed using the integral transform approach described previously incorporated U.S. Ser. No. 13/333,232 to provide a plurality of linear functionals, e.g., $\langle T_1^\omega \rangle$, Tapered areas. Porosity calculations which may be obtained by processing the NMR data G(t), or from other sources can be used as inputs to the integral transform approach processing. The linear functionals obtained are then used as constraints or "priors" in a cost function incorporating them as well as Laplace transform elements and utilizing indications of the NMR data in order to generate a $T_1$ distribution denoted by $f_{NEW}(T_1)$. The calculated $T_1$ distribution may be used for any of many purposes such as (by way of example only) to generate an estimate of one or more parameters of the sample. Where the sample is a rock or a formation, the parameters may include parameters such as rock permeability and/or hydrocarbon viscosity, bound and free fluid volumes, among others. The parameters may then be used, if desired, in models, equations, or otherwise to act on the sample, such as in recovering hydrocarbons from the formation.

It will be appreciated by those of ordinary skill in the art, that when minimizing a cost function with respect to a longitudinal relaxation time ($T_1$) to obtain a $T_1$ distribution estimation $f(T_1)$, equation 1 can be modified to $$G=(t)=\int_0^\infty P_\tau(T_1)e^{-t/T_1}f(T_1)dT_1, \quad (13)$$

where the function $P_\tau(T_1)$ depends on the pulse sequence of the NMR equipment used to probe and measure the sample. Now, if G is a vector containing indications of the NMR measurements made by an NMR tool on a sample (e.g., the data itself, the data in compressed form by means of the singular value decomposition or windows sum, or other indications of the data), and L is a matrix representing the discretization of the function in equation (13), and it is assumed that $N_m$ moments denoted by $\langle T_1^{\omega_i} \rangle$, i=1, ..., $N_m$, and $N_a$ areas denoted by $B_i$, i=1, ..., $N_a$ are estimated directly by means of the appropriate integral transforms on G(t) as described in previously incorporated Ser. No. 13/333,232, a cost function with respect to $f_{NEW}(T_1)$ may be minimized, $$\min_{f_{NEW} \geq 0} \|W(\bar{G} - \bar{L}f_{NEW})\|^2 + \alpha \|f_{NEW}\|^2 \quad (14)$$

where $f_{NEW}$ is a discretized vector version of an underlying density function $f_{NEW}(T_1)$, W is a covariance matrix of uncertainties in the parameters (as described in (12) above), $\alpha$ is a regularization parameter, $$\bar{G} = \begin{bmatrix} G \\ \langle T_2^{\omega_1} \rangle \\ \vdots \\ \langle T_1^{\omega_{N_m}} \rangle \\ B_1 \\ \vdots \\ B_{N_a} \end{bmatrix} \quad (15)$$

is an extended vector containing the indications of the measurements G as well as the constraints (moments $\langle T_1^{\omega_i} \rangle$ and areas $B_i$) generated by the integral transform approach, and $\bar{L}$ is the extended matrix, $$\bar{L} = \begin{bmatrix} L \\ \frac{1}{\phi}T_{1,min}^{\omega_1} & \cdots & \frac{1}{\phi}T_{1,max}^{\omega_1} \\ & \ddots & \\ \frac{1}{\phi}T_{1,min}^{\omega_{N_m}} & \cdots & \frac{1}{\phi}T_{1,max}^{\omega_{N_m}} \\ H(T_{c_1}, T_1) \\ \vdots \\ H(T_{c_{N_a}}, T_1) \end{bmatrix} \quad (16)$$

where L is a Laplace transform matrix with components $(L)_{ij} = P_\tau(T_{1,j})e^{-t_i/T_{1,j}}$, $\phi$ is the porosity, $H(T_c, T_1)$ represent the tapered Heaviside function varying smoothly between 0 and 1 with $H(T_c, T_1)=0.5$ when $T_1 = T_c$ as described in previously incorporated U.S. Ser. No. 13/333,232, and $T_{1,min}$ and $T_{1,max}$ represent the minimum and maximum value of the discretized $T_1$ vector so that for a given $T_1$ distribution $f_{NEW}$ with components $f_{NEW}(T_{1,i})$ the $\omega$-th moment is defined as $$\langle T_1^\omega \rangle = \frac{1}{\phi} \sum_{i=min}^{max} T_{1,i}^\omega f_{NEW}(T_{1,i}) \quad (17)$$

Thus, $\bar{L}$ contains Laplace transform elements as well as functions of the constraints.

It will be appreciated by those skilled in the art that any of many optimization routines may be utilized to solve the cost function of equation (14) for $f_{NEW}$.

In a similar manner, according to another embodiment, instead of minimizing a cost function with respect to a relaxation time to obtain a relaxation time distribution estimation, a cost function is minimized with respect to NMR diffusion (D) to obtain a D distribution estimation $f(D)$. More specifically, as in FIG. 1, data G(t) indicative of what might have been measured by an NMR tool as a result of having applied a pulse sequence to a sample, is processed using the integral transform approach described previously incorporated U.S. Ser. No. 13/333,232 to provide a plurality of linear functionals, e.g., $\langle D^{\omega_i} \rangle$, Tapered areas. Porosity calculations which may be obtained by processing the NMR data G(t), or from other sources can be used as inputs to the integral transform approach processing. The linear functionals obtained are then used as constraints or "priors" in a cost function incorporating them as well as Laplace transform elements and utilizing indications of the NMR data in order to generate a D distribution denoted by $f_{NEW}(D)$. The calculated D distribution may be used for any of many purposes such as (by way of example only) to generate an estimate of one or more parameters of the sample. Where the sample is a rock or a formation, the parameters may include parameters such as rock permeability and/or hydrocarbon viscosity, bound and free fluid volumes, among others. The parameters may then be used, if desired, in models, equations, or otherwise to act on the sample, such as in recovering hydrocarbons from the formation.

It will be appreciated by those of ordinary skill in the art, that when minimizing a cost function with respect to diffusion (D) to obtain a D distribution estimation $f(D)$, equation 1 can be modified to $$G(t) = \int_0^\infty P_\tau(D)e^{-tD}f(D)dD, \quad (18)$$

where the function $P_\tau(D)$ depends on the pulse sequence of the NMR equipment used to probe and measure the sample. Now, if G is a vector containing indications of the NMR measurements made by an NMR tool on a sample (e.g., the data itself, the data in compressed form by means of the singular value decomposition or windows sum, or other indications of the data), and L is a matrix representing the discretization of the function in equation (18), and it is assumed that $N_m$ moments denoted by $\langle D^{\omega_i} \rangle$, i=1, ..., $N_m$, and $N_a$ areas denoted by $B_i$, i=1, ..., $N_a$ are estimated directly by means of the appropriate integral transforms on G(t) as described in previously incorporated Ser. No. 13/333,232, a cost function with respect to $f_{NEW}(D)$ may be minimized, $$\min_{f_{NEW} \geq 0} \|W(\bar{G} - \bar{L}f_{NEW})\|^2 + \alpha \|f_{NEW}\|^2 \quad (19)$$

where $f_{NEW}$ is a discretized vector version of an underlying density function $f_{NEW}(D)$, $\alpha$ is a regularization parameter, $$\overline{G} = \begin{bmatrix} G \\ \langle D^{\omega_i} \rangle \\ \vdots \\ \langle D^{\omega_{N_m}} \rangle \\ B_1 \\ \vdots \\ B_{N_a} \end{bmatrix} \quad (20)$$

is an extended vector containing the indications of the measurements G as well as the constraints (moments $\langle D^{\omega_i} \rangle$ and areas $B_i$) generated by the integral transform approach, W is a covariance matrix of $\overline{G}$, and $\overline{L}$ is the extended matrix, $$\overline{L} = \begin{bmatrix} L \\ \frac{1}{\phi} D_{min}^{\omega_1} & \cdots & \frac{1}{\phi} D_{max}^{\omega_1} \\ & \ddots & \\ \frac{1}{\phi} D_{min}^{\omega_{N_m}} & \cdots & \frac{1}{\phi} D_{max}^{\omega_{N_m}} \\ H(D_{c_1}, D) \\ \vdots \\ H(D_{N_a}, D) \end{bmatrix} \quad (21)$$

where L is a Laplace transform matrix with components $(L)_{ij} = P_\tau(D)e^{-tD}$, $\phi$ is the porosity, $H(D_c, D)$ represent the tapered Heaviside function varying smoothly between 0 and 1 with $H(D_c, D) = 0.5$ when $D = D_c$ as described in previously incorporated U.S. Ser. No. 13/333,232, and $D_{min}$ and $D_{max}$ represent the minimum and maximum value of the discretized D vector so that for a given D distribution $f_{NEW}$ with components $f_{NEW}(D_i)$ the $\omega$-th moment is defined as $$\langle D^\omega \rangle = \frac{1}{\phi} \sum_{i=min}^{max} D_i^\omega f_{NEW}(D_i) \quad (22)$$

Thus, $\overline{L}$ contains Laplace transform elements as well as functions of the constraints.

According to other embodiments, the embodiments described above may be extended to extract multidimensional distributions such as (by way of example only) diffusion-$T_2$ distribution functions, diffusion-$T_1$ distribution functions and $T_1$-$T_2$ distribution functions. This may be done by one of ordinary skill in the art after reference to the previous embodiments and by reference to knowledge in the art such as described in M. D. Hurlimann and L. Venkataramanan, "Quantitative Measurement of Two-Dimensional Distribution Functions of Diffusion and Relaxation in Grossly Inhomogenous Fields," *Journal of Magnetic Resonance* 157, 31-42 (2002); Y.-Q. Song et al., "$T_1$-$T_2$ Correlation Spectra Obtained Using a Fast Two-Dimensional Laplace Inversion," *Journal of Magnetic Resonance* 154, 1-8 (2002); and R. L. Kleinberg et al., "Nuclear Magnetic Resonance of Rocks: $T_1$ vs. $T_2$," SPE 26470 (1993). Thus, by way of example, for a $T_1$-$T_2$ distribution function, the measured nuclear magnetic resonance (NMR) data resulting from a multi-component sample can be denoted by $G(t, \tau)$ which represents a multidimensional, multi-exponential decay, with time constants $T_1$ and $T_2$ and amplitudes $f(T_1, T_2)$ $$G(t, \tau) = \int_0^\infty \int_0^\infty P_\tau(T_2) e^{-t/T_2} e^{-t/T_1} f(T_1, T_2) dT_1 dT_2 \quad (23)$$

where the function $P_\tau(T_2)$ is referred to as the polarization factor and depends on the pulse sequence of the NMR equipment used to probe and measure the sample. Now, if G is a vector containing indications of the NMR measurements made by an NMR tool on a sample (e.g., the data itself, the data in compressed form by means of the singular value decomposition or windows sum, or other indications of the data), and L is a matrix representing the discretization of the function in equation (23), and it is assumed that $N_m$ moments denoted by $\langle T_1^{\omega_i} T_2^{n_j} \rangle$, i=1, ..., $N_n$ and $N_a N_b$ areas denoted by $B_i$, i=1, ..., $N_a N_b$ are estimated directly by means of the appropriate integral transforms on G(t) as described in previously incorporated Ser. No. 13/333,232, a cost function with respect to $f_{NEW}$ may be minimized, $$\min_{f_{NEW} \geq 0} \| W(\overline{G} - \overline{L} f_{NEW}) \|^2 + \alpha \| f_{NEW} \|^2 \quad (24)$$

where $f_{NEW}$ is a discretized vector version of an underlying density function $f_{NEW}(T_1, T_2)$, $\alpha$ is a regularization parameter, $$\overline{G} = \begin{bmatrix} G \\ \langle T_1^{\omega_1} T_2^{n_1} \rangle \\ \vdots \\ \langle T_1^{\omega_{N_m}} T_2^{n_{N_n}} \rangle \\ B_1 \\ \vdots \\ B_{N_a N_b} \end{bmatrix} \quad (25)$$

is an extended vector containing the indications of the measurements G as well as the constraints (moments $\langle T_1^{\omega_i} T_2^{n_j} \rangle$ and areas $B_i$) generated by the integral transform approach, W is a covariance matrix corresponding to $\overline{G}$, and $\overline{L}$ is the extended matrix, $$\overline{L} = \begin{bmatrix} L \\ \frac{1}{\phi} T_{1,min}^{\omega_1} T_{2,min}^{n_1} & \cdots & \frac{1}{\phi} T_{1,max}^{\omega_1} T_{2,max}^{n_1} \\ & \ddots & \\ \frac{1}{\phi} T_{1,min}^{\omega_{N_m}} T_{2,min}^{n_N} & \cdots & \frac{1}{\phi} T_{1,max}^{\omega_{N_m}} T_{2,max}^{n_N} \\ H(T_{c_{i1}}, T_1) H(T_{c_j}, T_2) \\ \vdots \\ H(T_{N_a}, T_1) H(T_{N_b}, T_2) \end{bmatrix} \quad (26)$$

where L is a Laplace transform matrix with components corresponding to $P_\tau(T_1) e^{-t/T_2} e^{-\tau/T_1}$, $\phi$ is the porosity, $H(T_c, T_1)$ and $H(T_c, T_2)$ represent the tapered Heaviside function varying smoothly between 0 and 1 with $H(T_c, T_1)$ and $H(T_c, T_2) = 0.5$ when $T_1 = T_c$ and $T_2 = T_c$ as described in previously incorporated U.S. Ser. No. 13/333,232, and $T_{1,min}$, $T_{2,min}$ and $T_{1,max}$ and $T_{2,max}$ represent the minimum and maximum value of the discretized $T_1$ and $T_2$ vectors so that for a given ($T_1$, $T_2$) distribution $f_{NEW}$ with components $f_{NEW}(T_{1,i}, T_{2,j})$ the $(\omega, n)$-th moment is defined as $$\langle T_1^\omega T_2^\omega \rangle = \frac{1}{\phi} \sum_{i=min}^{max} \sum_{j=min}^{max} T_{1,i}^\omega T_{2,j}^n f_{NEW}(T_{1,i}, T_{2,j}) \quad (27)$$

Thus, $\overline{L}$ contains Laplace transform elements as well as functions of the constraints.

According to other embodiments, the embodiments described above may be extended to extract multidimensional distributions such as (by way of example only) diffusion-T1-T2 distribution functions, diffusion-T1-T2 functions as a function of depth of investigation as well as diffusion-T1-T2 functions as a function of azimuth. This may be done by one of ordinary skill in the art after reference to the previous embodiments and by reference to knowledge in the art such as described in M.D. Hurlimann and L. Venkataramanan, "Quantitative Measurement of Two-Dimensional Distribution Functions of Diffusion and Relaxation in Grossly Inhomogenous Fields," Journal of Magnetic Resonance 157, 31-42 (2002); Y.-Q. Song et al., "T1-T2 Correlation Spectra Obtained Using a Fast Two-Dimensional Laplace Inversion," and L.Venkataramanan, Y. Q. Song and M. D. Hurlimann, "Solving Fredholm integrals of the first kind with tensor product structure in 2 and 2.5 dimensions," vol. 50, No. 5, May 2002 and N. Heaton et al., "4D NMR—Applications of the radial dimension in magnetic resonance logging," Petrophysics, 49, 2 (2008).

There have been described and illustrated herein several embodiments of methods for estimating distributions of NMR-related measurements. While particular embodiments have been described, it is not intended that the claims be limited thereto, as it is intended that the claims be as broad in scope as the art will allow and that the specification be read likewise. Thus, while particular moments and areas generated by using the integral transform approach were described as being included into the problem formulation, it will be appreciated that the problem may be formulated with other constraints. Also, while certain optimization routines were disclosed as being useful to solve the cost function $f$ or the distributions, it will be appreciated that other routines could be utilized. In addition, while the calculated distributions were described as being useful to find parameters of a rock or a formation such as rock permeability and/or hydrocarbon viscosity, and bound and free fluid volumes, it will be appreciated that the calculated distributions could be used to find other parameters of other types of samples, or other parameters of rocks or formation (e.g., saturates, aromatic, resin and asphaltene analysis of hydrocarbons, see M. D. Hurlimann et al "Hydrocarbon Composition from NMR Diffusion and Relaxation Data," Petrophysics, 50, no. 2, 116-129 (2009)). Furthermore, while the parameters were described as being used in models, equations, or otherwise to act on the sample, such as in recovering hydrocarbons from a formation, it will be understood that depending upon the parameters and the sample, they could be used in other manners. It will therefore be appreciated by those skilled in the art that yet other modifications could be made without deviating from its spirit and scope of the claims.

What is claimed is:

1. A method of investigating a sample, comprising:
performing nuclear magnetic resonance (NMR) measurements on the sample using an NMR tool to obtain NMR data;
conducting integral transforms on the NMR data to obtain linear functionals associated with said sample;
utilizing said linear functionals as constraints in a cost function which includes said NMR data, said linear functionals, and Laplace transform elements;
minimizing said cost function with respect to an NMR-related distribution to obtain a distribution estimation relating to the sample; and
using said distribution estimation to find values of at least one parameter of the sample.

2. A method according to claim 1, wherein:
said sample is a geological formation, and said at least one parameter includes at least one of permeability, hydrocarbon viscosity, bound fluid volume, and free fluid volume.

3. A method according to claim 2, further comprising:
using said at least one parameter in order to act on said formation to recover hydrocarbons from the formation.

4. A method according to claim 1, wherein:
said NMR-related distribution comprises at least one of $T_1$, $T_2$, and D, and said NMR distribution is one of a $T_1$ distribution estimation $f(T_1)$ where $T_1$ is a longitudinal relaxation time for protons in the sample, a $T_2$ distribution estimation $f(T_2)$ where $T_2$ is a transverse relaxation time for protons in the sample, and a D distribution estimate $f(D)$ where D is an indication of diffusion.

5. A method according to claim 4, wherein:
said NMR-related distribution is a multidimensional distribution comprising at least two of $T_1$, $T_2$, and D.

6. A method according to claim 4, wherein:
said minimizing said cost function comprises minimizing said cost function with respect to a $T_2$ distribution to obtain a $T_2$ distribution estimation $f(T_2)$ which is described by $\min_{f_{NEW} \geq 0} \|W(\overline{G} - \overline{L} f_{NEW})\|^2 + \alpha \|f_{NEW}\|^2$ where W is a covariance matrix of uncertainties in said linear functionals, $\overline{G}$ is an extended vector containing said NMR data and said linear functionals, $\overline{L}$ is an extended matrix containing Laplace transform matrix elements, $f_{NEW}$ is a discretized vector version of an underlying density function $f_{NEW}(T_2)$, and $\alpha$ is a regularization parameter.

7. A method according to claim 6, wherein:
said linear functionals comprise moments $\langle T_2^{\omega_i} \rangle$ and areas $B_i$.

8. A method according to claim 7, wherein:
said extended matrix is described by $$\overline{L} = \begin{bmatrix} L \\ \frac{1}{\phi} T_{2,min}^{\omega_1} & \cdots & \frac{1}{\phi} T_{2,max}^{\omega_1} \\ & \ddots & \\ \frac{1}{\phi} T_{2,min}^{\omega_{N_m}} & \cdots & \frac{1}{\phi} T_{2,max}^{\omega_{N_m}} \\ H(T_{c_1}, T_2) \\ \vdots \\ H(T_{N_a}, T_2) \end{bmatrix}$$

where L is a Laplace transform matrix with said Laplace transform elements $(L)_{ij} = P_\tau(T_{2,j}) e^{-t_i/T_{2,j}}$, $\phi$ is a porosity indication, $H(T_c, T_2)$ elements represent a tapered Heaviside function and $T_{2,min}$ and $T_{2,max}$ represent minimum and maximum value of said discretized $T_2$ vector so that for a given $T_2$ distribution f with components $f_{NEW,i}$, the $\omega$-th moment is defined as $$\langle T_2^\omega \rangle = \frac{1}{\phi} \sum_{i=min}^{max} T_{2,i}^\omega f_{NEW}(T_{2,i}).$$

9. A method according to claim 8, wherein:
said Heaviside function varies smoothly between 0 and 1 with $H(T_c, T_2) = 0.5$ when $T_2 = T_c$.

10. A method according to claim 7, wherein:
said co-variance matrix of uncertainties is described by $$W = \begin{bmatrix} \frac{1}{\sigma_\epsilon} & & & & & & \\ & \frac{1}{\sigma_{\omega_1}} & & & & & \\ & & \ddots & & & & \\ & & & \frac{1}{\sigma_{N_m}} & & & \\ & & & & \frac{1}{\sigma_{B_i}} & & \\ & & & & & \ddots & \\ & & & & & & \frac{1}{\sigma_{N_m}} \end{bmatrix}$$

where $\sigma_\epsilon$ is the standard deviation of noise in said NMR measurements, and $\sigma_{\omega_j}$ and $\sigma_{B_i}$ the estimated uncertainties in said moments and said areas.

11. A method according to claim 4, wherein:
said minimizing said cost function comprises minimizing said cost function with respect to a $T_1$ distribution to obtain a $T_1$ distribution estimation f ($T_1$) which is described by $\min_{f_{NEW} \geq 0} \|W(\overline{G} - \overline{L} f_{NEW})\|^2 + \alpha \|f_{NEW}\|^2$ where W is a covariance matrix of uncertainties in said linear functionals, $\overline{G}$ is an extended vector containing said NMR data and said linear functionals, $\overline{L}$ is an extended matrix containing Laplace transform matrix elements, $f_{NEW}$ is a discretized vector version of an underlying density function $f_{NEW}(T_1)$, and $\alpha$ is a regularization parameter.

12. A method according to claim 11, wherein:
said linear functionals comprise moments ($T_1^{\omega_i}$) and areas $B_i$.

13. A method according to claim 12, wherein:
said extended matrix is described by $$\overline{L} = \begin{bmatrix} & L & \\ \frac{1}{\phi} T_{1,min}^{\omega_1} & \cdots & \frac{1}{\phi} T_{1,max}^{\omega_1} \\ & \ddots & \\ \frac{1}{\phi} T_{1,min}^{\omega_{N_m}} & \cdots & \frac{1}{\phi} T_{1,max}^{\omega_{N_m}} \\ & H(T_{c_1}, T_1) & \\ & \vdots & \\ & H(T_{N_a}, T_1) & \end{bmatrix}$$

where L is a Laplace transform matrix with said Laplace transform elements $(L)_{ij} = P_\tau(T_{2,j}) e^{-t_i/T_{1,j}}$, $\phi$ is a porosity indication, $H(T_c, T_1)$ elements represent a tapered Heaviside function and $T_{1,min}$ and $T_{1,max}$ represent minimum and maximum value of said discretized $T_1$ vector so that for a given $T_1$ distribution f with components $f_{NEW,i}$, the $\omega$-th moment is defined as $$\langle T_1^\omega \rangle = \frac{1}{\phi} \sum_{i=min}^{max} T_{1,i}^\omega f_{NEW}(T_{1,i}).$$

14. A method according to claim 13, wherein:
said Heaviside function varies smoothly between 0 and 1 with $H(T_c, T_1) = 0.5$ when $T_1 = T_c$.

15. A method according to claim 12, wherein:
said co-variance matrix of uncertainties is described by $$W = \begin{bmatrix} \frac{1}{\sigma_\epsilon} & & & & & & \\ & \frac{1}{\sigma_{\omega_1}} & & & & & \\ & & \ddots & & & & \\ & & & \frac{1}{\sigma_{N_m}} & & & \\ & & & & \frac{1}{\sigma_{B_i}} & & \\ & & & & & \ddots & \\ & & & & & & \frac{1}{\sigma_{N_m}} \end{bmatrix}$$

where $\sigma_\epsilon$ is the standard deviation of noise in said NMR measurements, and $\sigma_{\omega_j}$ and $\sigma_{B_i}$ are the estimated uncertainties in said moments and said areas.

16. A method according to claim 4, wherein:
said minimizing said cost function comprises minimizing said cost function with respect to a D distribution to obtain a D distribution estimation f (D) which is described by $\min_{f_{NEW} \geq 0} \|W(\overline{G} - \overline{L} f_{NEW})\|^2 + \alpha \|f_{NEW}\|^2$ where W is a covariance matrix of uncertainties in said linear functionals, G is an extended vector containing said NMR data and said linear functionals, $\overline{L}$ is an extended matrix containing Laplace transform matrix elements, $f_{NEW}$ is a discretized vector version of an underlying density function $f_{NEW}(D)$, and $\alpha$ is a regularization parameter.

17. A method according to claim 16, wherein:
said linear functionals comprise moments ($D^{\omega_i}$) and areas $B_i$.

18. A method according to claim 17, wherein:
said extended matrix is described by $$\overline{L} = \begin{bmatrix} & L & \\ \frac{1}{\phi} D_{min}^{\omega_1} & \cdots & \frac{1}{\phi} D_{max}^{\omega_1} \\ & \ddots & \\ \frac{1}{\phi} D_{min}^{\omega_{N_m}} & \cdots & \frac{1}{\phi} D_{max}^{\omega_{N_m}} \\ & H(D_{c_1}, D) & \\ & \vdots & \\ & H(D_{N_a}, D) & \end{bmatrix}$$

where L is a Laplace transform matrix with said Laplace transform elements $(L)_{ij} = P_\tau(D) e^{-tD}$, $\phi$ is a porosity indication, $H(D_c, D)$ elements represent a tapered Heaviside function and $D_{min}$ and $D_{max}$ represent minimum and maximum value of said discretized D vector so that for a given D distribution f with components $f_{NEW,i}$, the ω-th moment is defined as $$\langle D^\omega \rangle = \frac{1}{\phi} \sum_{i=min}^{max} D_i^\omega f_{NEW}(D_i).$$

19. A method according to claim 18, wherein:
said Heaviside function varies smoothly between 0 and 1 with $H(D_c,D)=0.5$ when $D=D_c$.

* * * * *